(12) United States Patent
Monteiro

(10) Patent No.: US 11,173,303 B2
(45) Date of Patent: Nov. 16, 2021

(54) DEVICE AND MEANS TO AMELIORATE DISCOMFORT AND PAIN DURING DENTAL AND SIMILAR PROCEDURES

(71) Applicant: Sergio Lara Pereira Monteiro, Los Angeles, CA (US)

(72) Inventor: Sergio Lara Pereira Monteiro, Los Angeles, CA (US)

( * ) Notice: Subject to any disclaimer, the term of this patent is extended or adjusted under 35 U.S.C. 154(b) by 0 days.

(21) Appl. No.: 16/718,079

(22) Filed: Dec. 17, 2019

(65) Prior Publication Data

US 2020/0139119 A1    May 7, 2020

Related U.S. Application Data

(63) Continuation-in-part of application No. 15/641,302, filed on Jul. 4, 2017, now abandoned.

(60) Provisional application No. 62/358,108, filed on Jul. 4, 2016.

(51) Int. Cl.
*A61N 1/36* (2006.01)
*A61N 1/40* (2006.01)
*A61C 3/02* (2006.01)

(52) U.S. Cl.
CPC ............ *A61N 1/36021* (2013.01); *A61C 3/02* (2013.01); *A61N 1/40* (2013.01); *A61C 2203/00* (2013.01)

(58) Field of Classification Search
CPC .. A61C 3/02; A61C 2203/00; A61N 1/36021; A61N 1/40
USPC .......................................................... 607/48
See application file for complete search history.

(56) References Cited

U.S. PATENT DOCUMENTS

| | | | |
|---|---|---|---|
| 2012/0289823 A1* | 11/2012 | Lee .................... | A61N 1/36185 600/424 |
| 2013/0085551 A1* | 4/2013 | Bachinski .......... | A61N 1/36021 607/59 |

* cited by examiner

*Primary Examiner* — Nadia A Mahmood

(57) ABSTRACT

A device and means to decrease the pain associated with dental procedures as from dental drills, the probing scratching tool to detect cavities, the needle to inject anesthesia, the tool to extract nerve for root canal treatment, etc. The device uses electrical currents of both positive and negative polarity or alternating current.

20 Claims, 17 Drawing Sheets

Figure 1A:
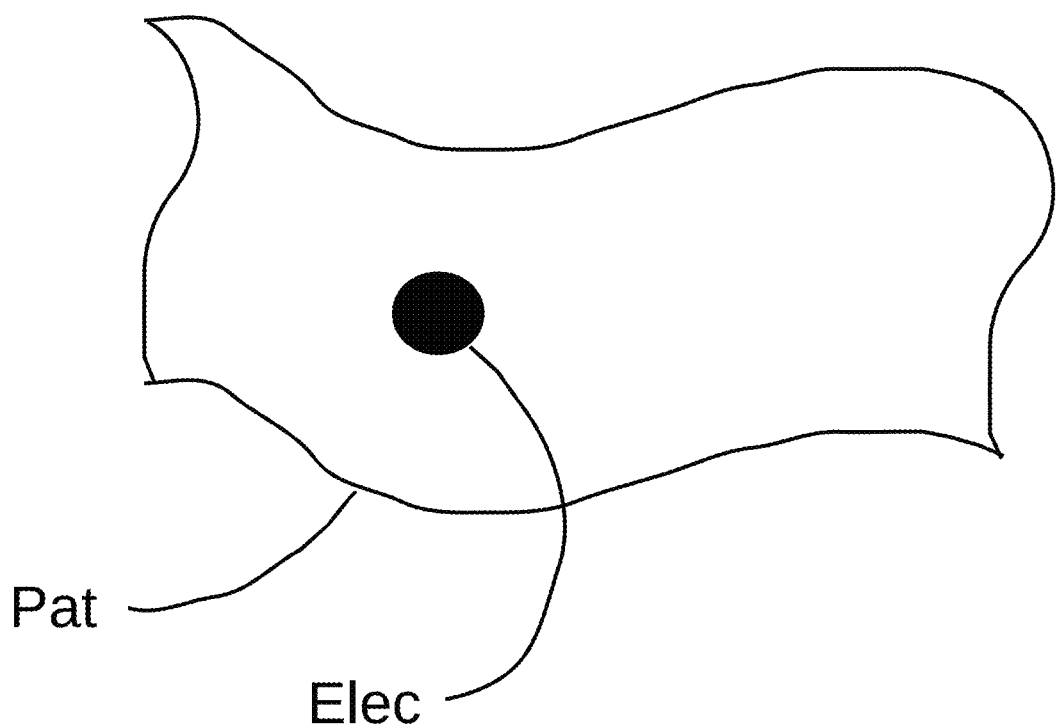

FIG. 5A
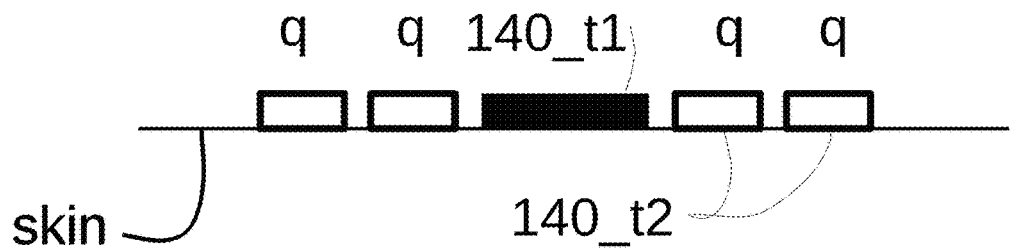
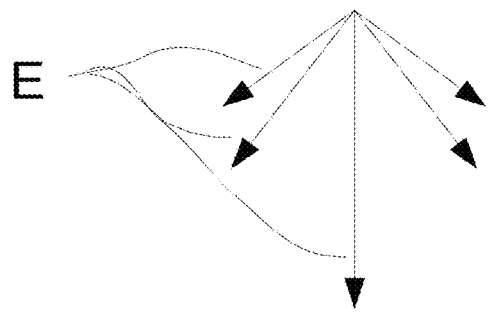
FIG. 5B
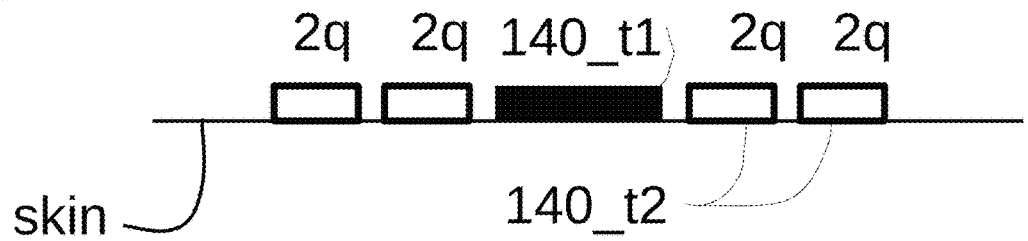
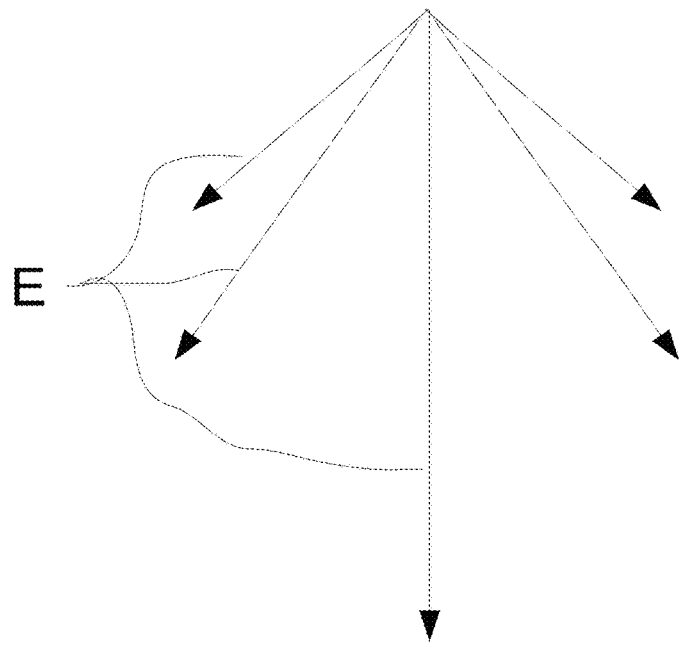

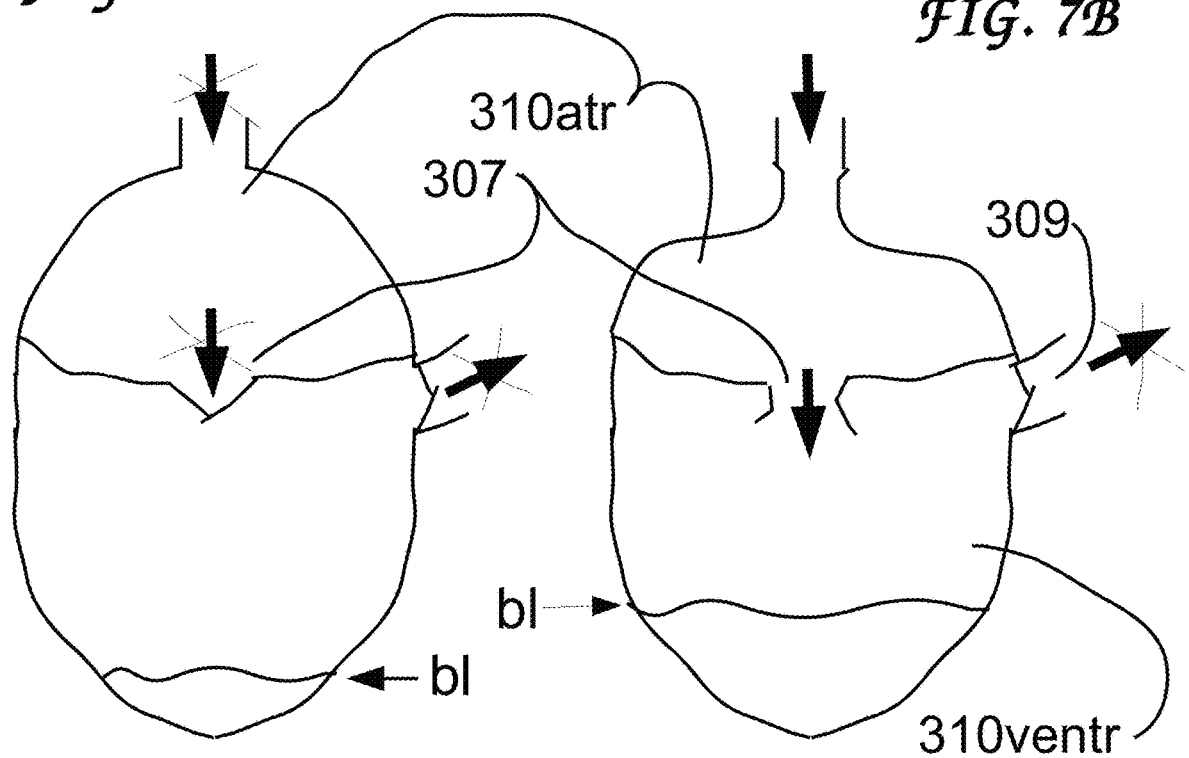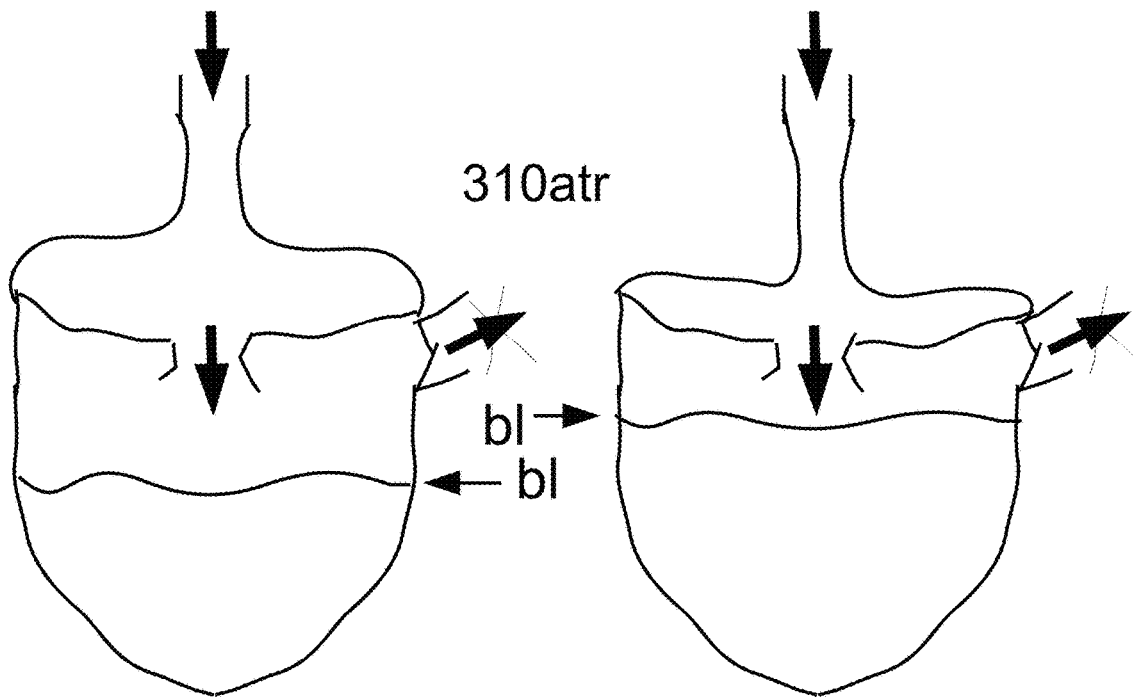

DEVICE AND MEANS TO AMELIORATE
DISCOMFORT AND PAIN DURING DENTAL
AND SIMILAR PROCEDURES

CROSS-REFERENCE TO RELATED
APPLICATIONS

This application is a continuation-in-part of patent application Ser. No. 15/641,302, application date 2017 Jul. 4. This application claims priority to US Provisional Patent Application Ser. No. 62/358,108, application date 2016 Jul. 4, entitled "Dirichlet's enveloping surface for field shaping with electrical stimulation of animal organs", to US Provisional Patent Application No. 62/114,038 dated 2015 Feb. 9, entitled "Cell electric stimulator with electrodes for electrical field shaping and separate electrode stimulation", to US Provisional Patent Application No. 62/027,116, application date 2014 Jul. 21, entitled "Piquita vector current with dedicated wires, distributed passive electrodes supercaps and surface electrodes", to US provisional patent application No. 61/881,997 dated 2013 Sep. 25, entitled "Cell electric stimulator with subsurface electrodes for electric field shaping and separate electrodes for stimulation", to US provisional application No. 61/486,179 dated 2011 May 13, entitled "Cell electric stimulator with randomized spatial distribution of electrodes for both current injection and for field shaping".

This application is related to U.S. regular patent application Ser. No. 15/019,969, application date 2016 Feb. 9, entitled "Cell electric stimulator with subsurface electrodes for electric field shaping and separate electrodes for stimulation", to U.S. regular patent application Ser. No. 14/540,989, application date 2014 Nov. 13, entitled "Animal and plant electrical stimulator with randomized spatial distribution of electrodes for both electric field shaping and for current injection", to U.S. regular patent application Ser. No. 14/495,871, application date 2014 Sep. 24, entitled "Cell electric stimulator with separate electrodes for electric field shaping and for stimulation" and to U.S. regular patent application Ser. No. 13/470,275, application date 2012 May 12, entitled "Animal and plant cell electric stimulator with randomized spatial distribution of electrodes for both current injection and for electric field shaping", published as US 2012-0289823 on 2012 Nov. 15 and now issued U.S. Pat. No. 8,954,145 on 2015 Feb. 10.

All of these are incorporated here by reference in their entirety.

FEDERALLY SPONSORED RESEARCH

Not applicable

SEQUENCE LISTING OR PROGRAM

Not applicable

BACKGROUND OF THE INVENTION

Field of Invention

This invention relates to electrical stimulation of cells in animals and other living forms, particularly to electrical stimulation of neurons in animals that are associated with the sensation of pain in general and to electrical stimulation of neurons at the mouth of animals that are associated with the sensation of pain in teeth. This invention offers a method and a device to ameliorate the pain at the hands of the feared dentist, as the needle used for the injection of anesthetics, during the probe of teeth for cavities, during the drilling of teeth to remove decayed teeth parts, in preparation for subsequent filling, during the removal of dental nerves, as for root canal treatment, and during the implantation of artificial teeth to take the place of extracted teeth. This invention also relates to electrical stimulation of heart cells, including heart muscles associated with heart muscle contraction, and the His bundle, the left and right bundles and the purkinje and similar fibers in hearts, and more precisely, it relates to the art of causing an efficient contraction sequence of the heart muscle in order to maximize the volume of blood pumped per unit of energy spent by the heart, known in medicine as the pumping fraction. It also relates to the art of electrical stimulation of the cochlea, as in cochlear implants. It also relates to the art of electrical stimulation of neurons as in brain and peripheral neurons. Brain neurons are stimulated both for clinical objectives, as in Parkinson's disease control, and in animal research as well, in which case neurons are stimulated to observe the consequences of the stimulation. It also relates to the art of electrical stimulation of organs, as stomach, etc. Electrical stimulation of the stomach and intestines can be for either appetite control or to control the stomach contraction, to achieve a better contraction sequence of the stomach and intestines, including a synchronized opening of the sphincter muscle that controls the exit of the food from the stomach into the intestine. It also relates to the electrical stimulation of muscles and tendons just below the skin, as is done by TENS devices. It also relates to controlling the pain for dental work.

Definition of Terms

Following the requirement of being precise with the description of the invention we start defining some key terms we use in the specifications to avoid any doubt on our meaning. Some of these terms are used in the ordinary sense of their use, some of these terms have double meaning (as in spoken language and in physics), some of these terms are of our creation to define our invention, and were not used before.

Active electrode—see type 1 electrode curved surface—we use this word in the generalized mathematical sense that includes a curve with infinite radius of curvature, which is a flat surface in normal speech.

Field-shaping electrode—see type 2 electrode.

first supporting devices—see pain-inflicting devices.

malleable sheet like supporting structure—A malleable structure capable of supporting a plurality of active and/or field-shaping electrodes, also possibly supporting wires, electrical energy sources and supporting electronics. Usually these malleable sheet like supporting structure have similar bending capability as a piece of fabric, as the ones used to make ordinary clothing, and they may be made of a variety of materials, as cotton, wool, silk, nylon, rubber or rubberized materials, and many others.

rigid penetrating devices—see pain-inflicting devices. Any device used during a dental procedure capable of being introduced into an existing cavity (as a tooth cavity) or of creating a cavity (as a drill that takes away decayed tooth matter).

Pain-inflicting devices—any device that inflict pain on an animal. In this context the pain-inflicting devices are most often either a needle used to inject anesthetics near the nerves and teeth of a patient, or a sharp pointed device used to scratch the teeth surface to inspect for cavities, or a drill used to take away decayed teeth tissues, or any of a multiplicity of tools used to extract a nerve for a root canal treatment, or any similar device. These pain-inflicting devices are also called here as first supporting devices and/or rigid penetrating devices TENS—Trans Electric Neural Stimulation, a known device used mostly by chiropractors but by other medical practitioners as well.

Type 1, or T1 or active electrode—these are the ordinary electrodes used by the existing devices which are capable of injecting electric current in their environment. They are referred in the figures as 140_t1. Cf with type 2 or field-shaping electrodes.

type 2, or T2, or field-shaping electrodes—these are electrically insulated electrodes which are not capable if injecting electric current in their environments yet are capable of projecting an electric field in their environment. They are referred in the figures as 140_t2. Cf with type 1 or active electrode.

Discussion of Prior Art

Electrical stimulation with the objective of alleviating pain for dental treatment has been known and used from before the christian era, as per review article by V. Kasat et al. "Transcutaneous electric nerve stimulation (TENS) in dentistry—a review" J. Clin. Exp. Dent. 2014, v6, pg 562:

"Brief History

"Electricity has been used for alleviation of pain since the era of ancient Greeks, Romans and Egyptians who used live Torpedo marmorata [electric ray], a type of electric fish for pain relief. In modern era, John Wesley in 18th century introduced electrotherapy for the relief of pain from sciatica, headache, kidney stone, gout, and angina pectoris. Use of electricity for relief of dental pain was first described in 19th century by a physician named Francis. In 20th century, various dental handpieces that provided an electrical current to the tooth via the bur were used to relieve pain during cavity preparation. After a lot of research, TENS or electronic dental anesthesia as it is called in dentistry has established itself as an anesthetic agent".

In this V. Kasat et al. Review article the reader can get a general idea of the current state of the art (almost, 2014) of the use of electrical stimulation for the purpose of alleviating pain during dental work.

Electrical stimulation for dental procedure is today an area of active research, as per clinical trial NCT03779659 that is just starting in December 2019 under the auspices of the National Institute of Health of the United States: ClinicalTrials.gov Identifier: NCT03779659, the details of which can be read at the website https://clinicaltrials.gov/ct2/show/NCT03779659#wrapper (accessed 14 Dec. 2019).

All these devices use standard TENS hardware, which is one or more electrodes, of the type used for EKGs, attached either to the person's outer skin or, less often, to the inner skin inside the mouth or even to the tongue. Our invention improves on these devices with the introduction of the obvious use of the very device that causes pain to deliver the soothing electric current as well: the probing tool that scratches the tooth as part of the procedure to inspect for cavities, or the drill, or the tool used to extract the nerve during root canal treatment, or the pliers or similar instrument used to extract a tooth from the unfortunate animal, whether human or non-human, or the needle penetrating the inside of the mouth to inject some anesthetics before the real thing. These pain-inflicting devices are also called here as first supporting devices and/or rigid penetrating devices Just think of it: the use of the very pain-inflicting element to deliver the soothing electric current is the best choice, because the pain-inflicting tool necessarily injects the current directly to the pain-sensing nerves ahead of its offense! I am so clever, ain't I?

Once the pain-causing element injects electric charges from type-1 electrodes onto the space surrounding it, especially the very tip of the pain-causing element, these injected charges may be guided by either type-2 electrodes surrounding the type-1 electrode on the pain-causing element or by type-2 electrodes somewhere else. This somewhere else is then a second location also involved in the electrical stimulation process. For the dental case this set of electrodes at this second location, also referred here as second supporting device, is likely to be a malleable sheet, adapted to conform to the curvature of the cheek of the patient or to some other body part of the patient, as the neck, the chin, the head, etc., which is fitted with both type-1 and/or type-2 electrodes. FIGS. 1 (A, B and C) show some options for these second supporting devices. FIGS. 5 (A and B) show some of the electric fields created by some variations of these second supporting devices, and FIGS. 10 (A, B, C, D, and E) show more variations of the shape of the electric fields possible to create with the type-2 electrodes. The type-1 electrodes on such a malleable sheet attached to the cheek of the patient may also guide the electric charges injected by the pain-causing element, either by attracting them (in this case the type-1 electrode at the second location has opposite polarity, or sign, to the polarity of the charges injected by the pain-causing element) or by repulsing them (in this case the type-1 electrode at the second location, the cheek, has the same polarity, or sign, as the electrode injecting charges at the pain-causing element). In either case, the type-2 electrodes are electrically insulated and cannot inject electric charges, as described elsewhere in this patent application, but are capable of creating an electric field in the space surrounding the pain-causing element, which electric field causes an electric force on the electric charges injected by the type-1 electrodes at the pain-causing element. It is up to the user to then create the electric potentials that cause the desired force on the injected charges that direct these latter (injected electric charges) to follow a desired path—which is the path that "rubs" on the pain-sensing neurons, fooling these pain-sensing neurons into not sending the pain sensation to the brain—hahah . . . I must end this paragraph with the warning to the reader that, to the best of my knowledge all the existing TENS devices use only type-1 electrodes, so all the argument above about type-2 electrode are valid for the enhanced devices introduced by the inventor here and in earlier beautiful and innovative patent applications by the inventor.

It is to be noted that both these first and/or second supporting devices are intended to be used during dental procedures which lasts no more than one hour on average, no more than 12 hours at maximum—god forbid longer than 12 hours dental procedures! This includes the rigid penetrating devices (first supporting devices) and the supporting TENS surfaces (second supporting devices at the second location). It is also to be noted that while the first supporting devices are formed as a rigid penetrating device, the second supporting devices are of a different form, perhaps a volumetric structure, perhaps a surface structure, which may be planar or non-planar, perhaps a linear structure. Also, most often, but not necessarily so, the second supporting devices are not of a rigid penetrating type, but generally these second supporting devices just conform to the shape of a surface or of a volume of interest, generally to either work in tandem with the first supporting devices (rigid penetrating devices), attracting or repelling the electric charges injected by these rigid penetrating devices, or also to support in location a plurality of type-2 electrodes with the objective of creating a desired electric field in the volume around them all, that is capable of guiding the injected electric charges towards the pain-sensing nerves to "fool" the pain-sensing nerves into not noticing what is happening. It is understood that the second supporting devices have to be fitted with some means to attach them to the desired position in the animals' body. These means may be, among others, velcro or buttons or zippers or glue or Frankenstein-type stitches or others, anything that keeps the second supporting devices fixed on the desired locations. As for the shape, these second supporting devices may assume any shape that is convenient, as a head cover, a bandana, a scarf, a cover around a cylindrically shaped part, as the ones used to measure the blood pressure that go around the upper arm then closes in place, usually with a velcro, or the closing fabric or the like used at the belly to prevent herniation on workers having to lift heavy weight at working, and any similar surface. A particularly important shape is a second supporting device that is adapted to be attached to the cheek of the animal (the person, usually), given that one of the main applications of this device is for dental procedures. It is understood that for the invention to operate there is a need for either an electric cell or a battery or the electricity may be taken from the mains (from the wall outlet), with or without a transformer to change the electric potential (known in US as "voltage"). The invention can operate with both AC and/or DC. The former option (AC) may offer advantages in that charges would not accumulate around the point of insertion, but would instead move to-and-from, but there are work around this, which are known to the persons familiar with the art of electrical stimulation of tissues, as DBS, etc., so this detail is not discussed here because it is known in the art. Wires are needed to connect the electrical energy source to the electrodes, which are not shown either, for the same reason. Many drills are ceramic and some of these are non-conductive, but conductive filaments can be manufactured inside a non-conductive ceramic drill, etc., and there are electric conductive ceramics and metallic conductive drills or from other materials, and etc. These and other options are available and are not discussed here for being known in the art of material sciences and old art, not related to the invention disclosed here.

Our invention has several other applications too, as for the heart. The heart is divided into four chambers: left and right atria, at the upper part of the heart, and left and right ventricles, at the lower part of the heart. Right and left are arbitrarily assigned to be from the point of view of the person—which is the opposite left-right from the point of view of the observer looking at the person from the front. The atria are more holding chambers then actually pumping devices, evolved to quickly fill up the ventricles, below them, and consequently their walls are thinner when compared with the lower part, the ventricles. The right heart is responsible for the pulmonary circulation, receiving venous (non- or little-oxygenated) blood from the full body at the right atrium, passing it down to the right ventricle below it, from where the blood is pumped to the lungs. This corresponds to a short path, to the lungs and back. Back from the lungs, the blood enters the left atrium, which holds some oxygenated blood volume then releases it down to the left ventricle below it, from where the blood is then pumped to the whole body. The left heart pumps blood to the whole body, which involves more work when compared with the shorter path from the right heart to lungs and back, so the left atrium has thicker, stronger walls. These considerations on the wall thickness are of importance on our invention, because our invention deals with the optimization of the pumping mechanism of the heart, which is heavily dependent on the propagation delays of the electrical pulses, through the heart muscles, that causes the pumping mechanism, as explained below. This, in turn, the delays of the electrical pulses as they propagate through the heart muscles depend on the local resistance along the propagation path, which depend on the muscle thickness (larger on the left side than on the right side), cell composition, and other factors. These factors are only in principle possible to measure, but in practice it is not possible to measure, so the best propagation path and sequence needs to be determined by trial-and-error on a system that it is safe to say that have no closed form mathematical solution—though the equations are well known, besides being actually simple in form and short in length.

The electrical nature of muscle contraction was first observed in the waning years of the 1700s by Luigi Galvani, who noticed that a frog's leg contracted when subjected to an electric current. Today it is known that all our muscles, from a blinking eye to a walking leg, to the motion of the fingers that press the keyboard keys to type this very text, work on the same principles observed by Galvani—including out heart. The heart contracts as response to an electric pulse, which is injected on it at the required frequency, which varies according to the person's activity and state of excitation. It is crucial here to keep in mind that this electric pulse does not propagate as the ordinary power in copper wires, which occurs very fast, virtually instantaneously from the human point of view, but propagates rather as a displacement of heavy ions inside and outside of the muscle cells, subjected to much scattering and other obstacles. In fact, the time elapsed between the initial contraction of the atrium, or upper heart chamber, and the ventricle, or lower heart chamber, is of the order of 120 to 200 ms—a rather long time for electronics events (long enough for an electric pulse on a power line to go completely around the earth. Of course that 120 ms, which is approximately $\frac{1}{10}$ of a second is still instantaneous from the point of view of human perception. It is, nevertheless, so much longer than the times in which electronics work, that it lends itself to easy manipulation by implanted artificial electrodes. This slow propagation of the electrical pulse in the heart muscle is important for the working of our invention, so the reader is requested to keep this in mind.

Several malfunctions are possible to occur that hinder the proper functioning of the heart. Some are of a mechanical nature, a subject not bearing on our invention. Others are of an emotional nature, as a broken heart, which cannot be solved by our invention either. But some malfunctions are of an electrical nature, which is the focus of our invention, as described later on: our invention is an inventive method and means to cause a better propagation of the electric pulse that causes the heart to beat—and consequently, our invention is an inventive method and system to cause a better heart pumping.

Given that a proper understanding of the mechanism of heart beating and of the propagation of the electrical pulse that determines it is crucial to the understanding of our invention, we proceed to a brief explanation of the mechanism of the heart beating. This is also necessary because our invention is based on two separated and insulated fields of knowledge: medicine & physiology, on one side, and electrical engineering, on the other side, which are separately well understood by two groups of persons, but hardly by the same individual.

There are a wealth of books on the subject. One example of a simplistic book that gives the non-medically trained reader an introduction to the subject is Thaler (2003), where the reader with a non-medical background can get more information, even though a simplistic one. In short, most muscles capable of contracting are made of such cells that under normal conditions they have an excess of negative ions inside their cellular walls, which causes an excess of positive ions just outside their cellular walls, attracted there by ordinary electrostatic attraction. When in this condition, its normal condition, the cell is said to be polarized. If the cell loses its inner negativity, the language of electrophysiology describes this as a depolarization event. We here warn the reader that this is a poor choice of name, a word that caused no end of confusion in my head until I figured out what they meant, because the cell is still polarized when the electrophysiologists mention a depolarization event, but it becomes polarized on the opposite direction (positive inside it), and my personal confusion is still not solved because to this day I do not know if the cell really becomes positively polarized, or if it simply becomes less negative. By a sequence of well-know mechanism this acquisition of positive charges (depolarization as said in the trade, misnomer as it is) causes the cell to contract, that is, to decrease its length. This is the mechanism behind the blinking of our eyes, behind our walking, behind my typing now—and also behind the heart contraction—probably including broken heart events. It being an electric phenomenon, this event can be controlled by the injection of the appropriate electrical pulse in the heart muscle. This will be described in the sequel, and our invention bears on a twist on the man-made mechanism (heart pacemaker) designed to cause a heart pumping contraction sequence. Our invention improves on the propagation of the artificial electric pulse that causes a heart contraction (and consequent blood pumping).

As a last preparation information we want to clarify that the heart pumping mechanism is a modification of a class of pumps called peristaltic pumps, which causes the motion of the fluid, or pumping, with a progressive forward squeezing of the container, which forces the fluid forward. If the reader is unfamiliar with the mechanism of peristaltic pumping, we recommend that she acquaints herself with the method, perhaps observing the animation in today's wikipedia article on peristaltic pump, or any similar source. The reader is requested to keep this fact in mind as he reads the explanation of our invention, that the hearts functions with a progressive squeezing of its chambers, akin to the milking of a caw, during which process the milker progressively squeezes the caw's tit between its pointing finger and the thumb, then press the middle finger, squeezing the stored liquid further down from the tit, then the annular than the little finger, at which point all the can be squeezed is out, the hand is opened to allow more milk to enter the fit and the process is repeated.

The reader must be warned too that though every cardiologist will always state that the heart pumps sequentially, many a cardiologist that states this mean only that the atrium contracts first, then the ventricle contracts after, then repeat the same cycle, unaware that within each of the two cycles the actual contractions is sequential in the sense that the muscles start contracting at one extremity (say, the top of the atrium) then sequentially contracting down, toward the exit valve at the bottom. This latter sequence is the one the inventors want to bring forth—and a sequence that, alas, many a cardiologist will deny.

In short, most of the heart cells are part of the miocardium, which is a variety of a large group of other cells which are capable of contracting when subjected to the mechanism just described of depolarization. The pumping sequence consists of blood entering the heart at the top of the atrium (which is also the upper chamber), then a sequential downward pumping squeeze of the atrium which squeezes the blood into the lower ventricle. Then there is a problem, because the exit of the ventricles is at its upper part, next to the entrance port from the atrium: both entrance and exit ports are next to each other, both at the top of the ventricles. Therefore, if the squeezing continued downward through the ventricles there would be no place for the blood to go (no exit port at the bottom of the ventricle!). This problem is solved with the interruption of the downward propagating electric pulse at the intersection of these two chambers and a re-emission of another pulse through fast channels known as His fibers, left and right bundles and finally the Purkinjie fibers which release the electrical pulse at the base of the ventricle, which then begin squeezing from bottom to top, squeezing the blood upwards towards the exit port (the pulmonary vein at the right ventricle and the aorta at the left ventricle). This is a clear design flaw.

So, the heart's electrical system starts with an electrical pulse at the top of the right atrium, from a small group of cells known as the sino-atrial node (SA node or SAN), from where it propagates fast to the left atrium by special fibers that propagate the electric pulse better than the miocardium muscle does, which causes a downward contraction of the atrium, the right atrium first, then the left atrium a few milliseconds later. The electric pulse, which has been propagating downwards is then captured at the base of the atrium, preventing it from continuing down, it is then used by special cells called the atrial-ventricular node (AV node or AVN) to start a new pulse which is send through special conduits (special wires, so to say), known as the His bundle, then the right and left bundle branch, then the Purkinjie fibers, which then release the electrical pulse regenerated at the atrio-ventricular node AVN at the lower part of the ventricles, causing now the ventricle to start contracting upwards, as needed to pump the blood to the upper exit port of the ventricles. This completes the heart cycle.

Electrical malfunctions of the heart may be more obvious faults as insufficient energy in the electrical pulse that causes the pumping or some more subtle ones as errors in the propagation of the electrical pulse. Our invention inserts itself in this latter category, it being a device to control the propagation of the electrical pulse through the heart muscles, therefore to control the sequential contraction of the heart muscle in the broader sense we use the concept here, that is, the continuously progressive contraction of the heart muscle, cell-to-cell, from the blood entry port to the blood exit port. The original artificial heart pacemakers simply injected an electric pulse near the sino-atrial node SAN at the top of the right atrium, and later versions injected two or even three separate pulses in two or three different parts of the hearts, with the appropriate time delays, which correspond to the elapsed time for the natural pulse to be at that place for a good contraction sequence. None of them, though, even attempted to control the path of the injected current once it is injected artificially—which is the object of our invention. In other words, our invention improves on the electrical propagation features of the electric pulse created by the artificial heart pacemakers, and in doing so it improves the squeezing sequence of the heart, which in turn improves the pumping efficiency. It is to be remembered that, because the heart is a variation of a peristaltic pump, the pumping sequence is of fundamental importance for an efficient pumping (the inventors hope that the reader did indeed go see the animation in Wikipedia).

Originally heart pacemakers were simply an exposed wire tip, the wire connected to a battery and electronics circuitry to create pulses of appropriate frequency, shape and amplitude. The original implant was made with an open chest surgery, but this was quickly supplanted by a less invasive and much less traumatic technique, with which an incision was made on some vein at the chest (usually the subclavian vein, on the upper chest), where a wire was inserted, which had some sort of screwing or anchoring ending at its distal extremity, then this wire was fed in until its distal extremity reached the upper right heart chamber, from the inside (the right atrium), where the wire tip was screwed on the inner part of the heart, near the natural starting point of the electrical pulse that causes the heart to beat, know as the sino-atrial node (SA node or SAN). During this process the patient is in an X-ray imaging system and the surgeon can observe the advancement of the wire down the vein on an X-ray monitor. The proximal end of the wire was then connected to a battery and electronics box which was implanted in the chest, in some convenient location. From the wire tip anchored at the distal end, a current emanated, which then propagated through the heart muscle, causing the muscle to contract as the current proceeded along it, hopefully similarly to the naturally occurring electric pulse. It is crucial here to remember that this muscle contraction occurs because of the electric charge carried by it, and consequently, it is the electric current propagation time and pathway that determines the heart contraction sequence—because the muscle cells contract as a consequence of the electric charge near it. The sequence of muscle contraction is crucial for an efficient heart functioning, because the heart must start squeezing from its furthest end, away from the discharge exit area, most away from the exit port, continuously squeezing its wall towards the exit port. The heart does not contracts as a person squeezes a tennis ball for exercise, but rather, the heart squeezes sequentially pushing the blood forward, towards the exit port. The reader can here recall the caw milking described above. Most people get astonished when they learn that the heart pumps not much more than 50% of the blood in it (approximately 70% for a healthy young person)—a rather low efficiency! Combining this astonishing low efficiency with the reverse of path direction of contraction discussed above, the conclusion is that the heart is poorly designed. So much for the American intelligent designer: intelligent he was not.

Over the more than 50 years of heart pacemaking, many types of electrode tips have been developed. Some of the electrode tips possessed some degree of symmetry, some not. Whether or not the tip electrode had or not symmetry, this quality was transferred to the current injected into the heart muscle. The heart, on the other hand, is asymmetric, particularly from the point of view of the point where the stimulating electrode is anchored in the heart, which often is near the sino-atrial node, or at the top of the right atrium. It follows that the current that is injected by current art heart pacemakers cannot follow well the contour of the heart muscle, causing a less than ideal contracting sequence. Other anchoring positions for the electrode are also used, and multiple electrodes as well, which may stimulate the atrium and the ventricle independently. Such is the reason behind the introduction of the introduction of the cardiac resynchronization therapy: a pulse at the top right (near the SAN), followed, with the appropriate delay by pulses at the bottom of both ventricles. But note that the resynchronization therapy fails to even try to go for the gold: to control the path and timing of the electric pulse propagation after the initial charge is injected! Our invention is exactly this—our invention goes for the gold.

In the former case, the tip symmetry had consequences on the current distribution in the heart muscle, because, at least initially, it caused a current symmetry. In the latter case, the lack of symmetry also had consequences on the current distribution, because it caused an initial asymmetric current injection, which could or could not be the ideal for the heart contraction sequence. In either case, the trajectory of current injection has not been controlled by prior art devices, which was a major problem as acknowledged by cardiologists working in the field of electrophysiology. This lack of control of the current distribution, as it propagated through the heart muscle, plagued all the earlier types of heart pacemakers, and still does in currently used heart pacemakers. Throughout the years, many variations were introduced in the electrodes, as the shape of the wire tip, which served to anchor it in place, but these changes were largely for mechanical reasons, as to provide a more secure anchoring of the electrode on the heart muscle, or to minimize physical damage to the heart tissues, etc. Changes have also occurred on the method of introducing it in the heart, but most of these were changes to solve other problems, not to induce a good squeezing sequence of the heart muscle. Consequently, the uncontrolled propagation of the electric current from the tip has been a constant. Attempts to improve the electric pulse propagation include the use of multiple wire tips, which injected current not only at different locations but also at different times, or with relative time delay between the stimulating places. Examples of such multiple site stimulation are atrial and ventricular stimulators, two tips, one at the atrium, another at the ventricle, which deliver a pulse with a time lag between them, corresponding to the time lag between atrial contraction and ventricular contraction. But these multiple stimulating tips are not designed to control the electric field—which determines the path of the injected electric current, which more or less follows the electric field lines because these are the force lines.

Such multiple electrodes, usually, though not consistently, worked better than a single electrode. Yet, this lack of optimization of the heart muscle contraction has been a major problem known to the electrophysiologists and heart specialists. This uncontrolled propagation was shared by most, if not all models and their variations, in spite of the fact that the cardiologists were aware that uncontrolled electric pulse propagation caused inefficient heart pumping. Cardiologists knew that they had to address the problem of electric pulse propagation through the heart, but they have so far not succeeded in this goal. In fact, the cardio guys have actually given up on this goal of controlling the electric charge propagation through the heart, with the goal of controlling the contraction sequence—it has been a mute point in the field! It has been a known problem in heart pacemakers, yet and amazingly, a problem which has defied solution for decades.

Moreover, even if multiple stimulating tips caused an improvement of the pumping squeezing sequence and efficiency, it had the detrimental effect of causing more muscle damage, as each anchored wire tip is a foreign body in the heart, also a foreign body which by necessity caused an injure to it, an injury which resulted in a scar tissue, which in turn has different electrical conductivity when compared with the normal heart, creating a problem spot for the very objective of controlled electric pulse propagation. Another problem was that, since often times the first attempt to anchor the tip in the endocardio is unsuccessful, either for mechanical or for electrical reasons, for every unsuccessful attempt the surgeon has to retract the tip then screw it again somewhere else, and occasionally even more than two attempts, each tip were usually responsible for multiple scars in the inner heart, which in turn posed limits to any dream of using a multiplicity of stimulating tips.

It seems that all currently used heart pacemakers attempt to solve the problem of electric pulse propagation inside the heart muscle tissues with the use of multiple electrodes, while nobody succeeded to control the current propagation, in direction and magnitude, using one single electrode for electric current injection. Nor have existing heart pacemakers made full use of multiple electrodes to more completely shape the electric field within the heart muscle—which is the same as the electrical current path, because the electric field lines are the same as the force lines, or the lines along which the injected charges move.

Currently used heart pacemakers simply used an arbitrarily shaped stimulating electrode, which than created a non-controlled electric field in the surrounding space, which in turn guided the injected charges (or electric current). Yet, because the electric pulse at the stimulating electrode is very short, for virtually all the heart cycle there exist no acting electric field to guide the propagation of electric charges. Our invention offers a method and a means to adjust the electric field, independently from the stimulating electrodes, to the best shape depending on the particular case, as needed.

Several authors have discussed the problem of guiding the electric charge injected in animal tissue for electrical stimulation [e.g., Butson and McIntyre "Current steering to control the volume of tissue activated during deep brain stimulation", Brain stimulation V. 1, pg. 7-15 (2008), Butson and McIntyre "Role of electrode design on the volume of tissue activated during deep brain stimulation" J. Neural Eng. V3 pg 1-8 (2006), Julia Buhlmann et al. "Modeling of a segmented electrode for desynchronizing deep brain stimulation" Frontier in Neuroeng. V 4, article 15 (December 2011)]. These and others calculate the impact of the electric field created by the stimulating electrodes to guide the electric charges injected by the same electrodes. It is implied that the effect occurs throughout the cycle, but the authors forget to notice that the electrodes are on for a very short time, so, even if the influence of the electric field is noticeable, the effect is fleeting, because the electrodes are off most of the time. A vivid analogy of the situation is the motion of the water along any river, which follows the channels that are directed to the ocean. In the case of the rivers the water is following the lines of the gravitational potential created by the planed earth underneath the path, while in the case of body cells electric stimulation the electric charges have to follow the electric potential created by any other electric charge that exist around the space in question. In the river's water case it is the gravitational force and the gravitational potential; in the electrical stimulation case, brain, heart and others, it is the electrical force and the electrical potential.

Of course that the stimulating electrodes by necessity create an electric field in the space surrounding them, which, in turn, cause a force on the electric charges injected by them, thereby applying a force, that is, guiding the path of the injected charges. What all the workers have so far failed to notice is that as long as they use the same electrodes for injecting charges and for electric field shaping, they run into a brick wall because the charge injecting electrodes are on for a very very short time (a very small duty cycle), which typically may be 2% for DBS as used for Parkinson's Disease control or even <<1% for artificial heart pacemaking. Once one takes notice of this, it follows that a solution for the goal of guiding the charges AFTER they have been injecting have to rely on electrodes that do not inject charges into the system. A solution to this conundrum was offered by one of us (SLPM) in U.S. Pat. No. 8,954,145, 10 Feb. 2015, titled "Animal and plant cell electric stimulator with randomized spatial distribution of electrodes for both current injection and for electric field shaping", where we disclosed a second type of electrode, which we then called passive electrodes but are now calling field shaping electrodes, largely because the word "passive" is used in electronics with a different meaning, meaning electronics components, as resistors and capacitors, that draw no power to exert their role, as opposed to what is known as active elements, like transistors and op-amps, which needs external power to be able to work. As defined by us, field shaping electrodes are electrodes that are unable to inject electric charges because they are covered by an electrically insulating layer. With this patent application we disclose an improvement on the field shaping electrodes described earlier at this U.S. Pat. No. 8,954,145.

OBJECTS AND ADVANTAGES

Accordingly, several objects and advantages of our invention are one or more of the following. A better squeezing sequence of the heart muscle, starting the muscle contraction from the end of the heart further away from the exit port, to the end of the heart closer to the exit port, for both the atrial and ventricle, with view to achieve a more efficient pumping, when compared with heart pacemakers in use today, which are designed with no intention to optimize the squeezing sequence.

Another object and advantage of our invention is that the field shaping electrodes allows for the maintenance and control of the electric vector field throughout the full pumping cycle—even after the electric charges are inserted. The field shaping electrodes offer improvement on both time and space.

Another object and advantage of our invention is to offer the ability to inject an electric current in the heart which causes a higher pumping fraction, which is a medical term meaning the fraction of the blood which is actually pumped out of the heart, or out of each chamber, when compared with the artificial pacemakers in use today.

Another object and advantage of our invention is to adjust the electric field over the heart muscle to take better advantage of the atrial ventricular node to cause a better squeezing sequence of the heart muscle when compared with artificial pacemakers in use today.

Another object and advantage of our invention is to adjust the electric field over the part of the heart muscle where the His bundle and the right and left bundles are, to control the propagation times of the electric current coming from the atrial-ventricular node to the bottom and sides of the ventricle, to cause a better squeezing sequence of the heart muscle when compared with the artificial pacemakers in use today.

Another object and advantage of our invention is to control the electric field where the Purkinje fibers are located, to take better advantage of the Purkinje fibers to cause a better squeezing sequence of the heart muscle when compared with the artificial pacemakers in use today.

Another object and advantage of our invention are a better volumetric fit of the neural electrical stimulation to the optimal heart and/or other tissues target volume, when compared with the heart stimulation devices in use today.

Still another object and advantage of our invention is the possibility of readjusting the field shaping electrodes after the initial heart electric pulse is generated at the SAN and a stimulating current has been injecting in the heart muscle, and while the electric pulse is still traveling through the heart tissues during the progression of the P-QRS-T contraction sequence, which lasts almost a full second.

A further object and advantage of our invention is to prevent electric charges from leaking out of the heart muscle into the phrenic nerve, known as phrenic nerve capture, which causes unwanted contractions of the diaphragm muscle between the chest and the abdomen.

Another object and advantage of our invention is to better control the electric field around the supporting structure from where electrical stimulation is injected in the target volume of the brain when performing Deep Brain Stimulation, to cause that the electrical stimulation reaches a larger volume of the target volume while better avoiding stimulating other parts of the brain that are near but outside and beyond the target volume.

Another object and advantage of our invention is the possibility of time control of stimulation sequences in neural stimulation, which is not achieved with devices in use today.

Another object and advantage of our invention is a better control of the shape of the volume of neurons that receive electrical stimulation in brain stimulation, as in DBS (Deep Brain Stimulation).

Another object and advantage of our invention is a better control of the shape of the volume of neurons that receive electrical stimulation in neural stimulation, as for TENS (Tanscutaneous Electrical Neural Stimulation) pain control.

Another object and advantage of our invention is a better control of the shape of the superficial distribution of neurons as for pain control in TENS (Transcutaneous Electrical Neural Stimulation) devices, Another object and advantage of our invention is a better control and shape of the mostly planar electrical stimulation of neurons as used in some cortical brain stimulation.

If one or more of the cited objectives is not achieved in a particular case, any one of the remaining objectives should be considered enough for the patent disclosure to stand, as these objectives and advantages are independent of each other.

Further objects and advantages of my invention will become apparent from a consideration of the drawings, the summary, the description of the invention and its variations, and the claims.

SUMMARY

It is well known in cardiology that the heart pumping efficiency is a direct consequence of a proper propagation, in time and space, through all available electrical paths in the heart cells, of the electrical pulse that causes the heart contraction, including the contraction sequence. This is acknowledged to be true whether the electrical pulse is the natural one starting at the SAN (sino-atrial node) or an artificial one, starting at the anchoring position of an artificial heart pacemaker. It is interesting to note here that evolution does not, and in fact cannot progress along modifications on the heart design toward the most efficient possible pumping, but only to the most efficient pumping from the existing configuration—which may well be incompatible with the best solution. It is not true that all that the heart that has been evolved by natural selection is the best solution,—and in the case of the heart contraction it is not the most efficient pumping. Moreover, even if nature had evolved the best possible contraction sequence, the artificial heart pacemaker does not inject the electric current at the same location as the natural pacemakers, and consequently the artificial heart pacemaker should correct for this variation. Finally, due to the asymmetry of the heart muscle, it would not be expectable that the currently used symmetric electrode would best substitute the natural pacemaker. Consequently, what is needed is a heart pacemaker that could maximize the pumping efficiency. Such a goal has eluded the practitioners because of a lack of mechanism for precise control of the current injection, in position, direction and relative timing, of the electrical stimulation. A timid step in the right direction is cardiac resynchronization therapy, which uses three independently controlled electrodes that fire at different times within the heart cycle with the objective of, starting anew three times, with the appropriate time delay, to produce a better electrical pulse propagation sequence—and remember here that the electrical pulse propagation sequence is the contraction sequence too!

Our invention is a step in the direction of better control of this stimulating pulse. Our invention discloses a mechanism to control the magnitude and the direction of the current in the heart muscle, also time delays between current injected from different locations on the surface of the stimulator; in other words, our invention affords the possibility of controlling the vector current, and the relative time at different directions and places, as opposed to only its magnitude (that is, the total injected electric current), as in existing heart pacemakers. Our invention also applies to other electrical stimulations as brain (DBS and cortical stimulation), spine, skin (as for TENS devices), cochlea (as for hearing aids), stomach (as to control stomach functions), and others.

Finally, our invention discloses a new type of electrode, the field-shaping electrodes, marked in the figures as 140_t2. The field shaping electrodes are electrically insulated, which means that they are unable to inject electric charges into the surrounding region. This is crucial for the implementation of the system. Indeed, it has been noticed before that the very electrodes that cause the electrical stimulation do create an electric field in the surrounding space, which in turn act on the injected charges, applying a force on them (Coulomb force). But for most situations these electrodes can be on for a very short time, which is particularly so for DBS and heart pacemakers, not so much for TENS. We disclose an insulated electrode which can be on continuously if so derided, because they do not inject electric charges in the surrounding region. This and other characteristics of the field shaping electrodes will be discussed in the following paragraphs, together with several variations of the shape and how to use them for different applications, as TENS, heart pacemakers, DBS, and more.

DRAWINGS

FIG. 1A—A malleable sheet like supporting structure (Pat) with one single electrode.

Figure 1B:
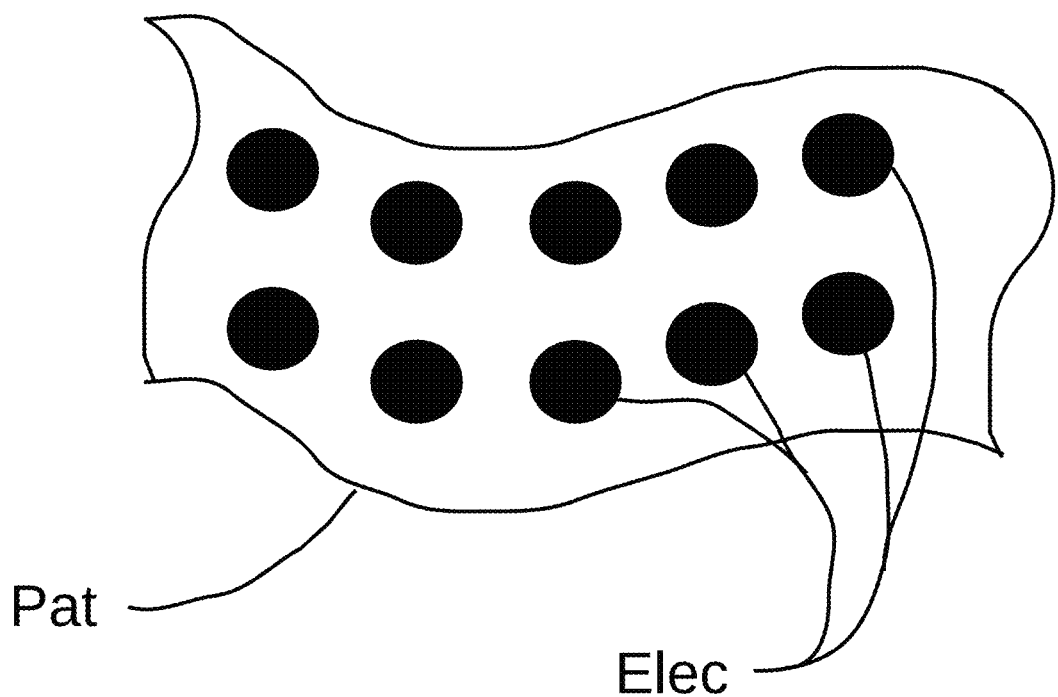

FIG. 1B—A malleable sheet like supporting structure (Pat) with several electrodes.

Figure 1C:
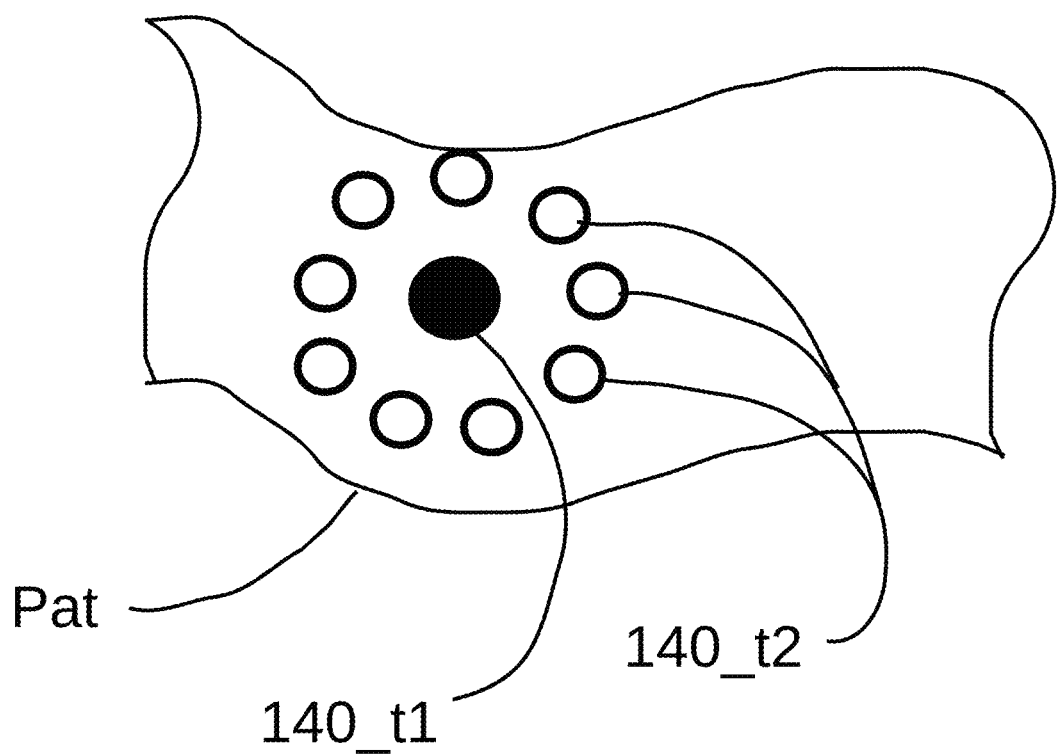

FIG. 1C—A malleable sheet like supporting structure (Pat) with both active and field shaping electrodes.

Figure 2:
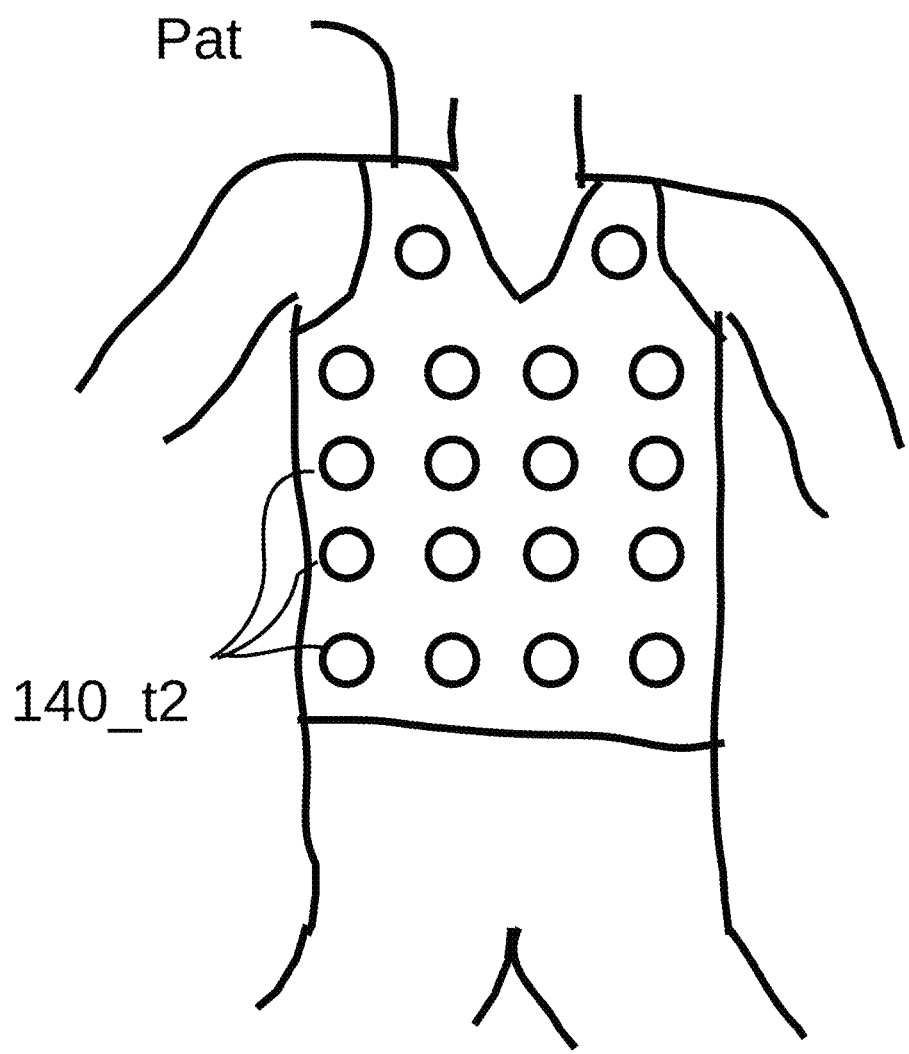

FIG. 2—A Dirichlet shirt with electrodes.

Figure 3:
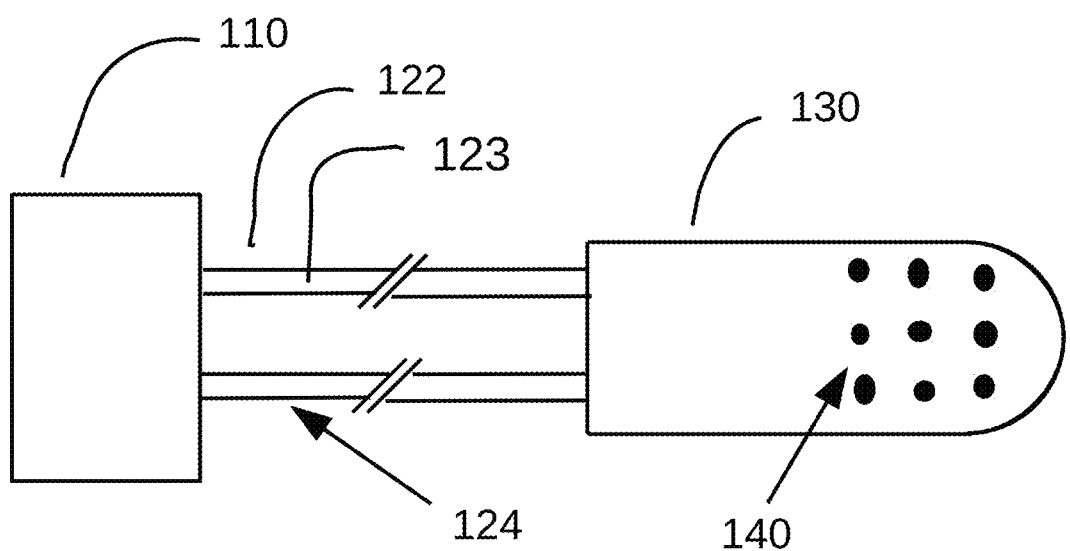

FIG. 3—a DBS type of electrical stimulator.

Figure 4:
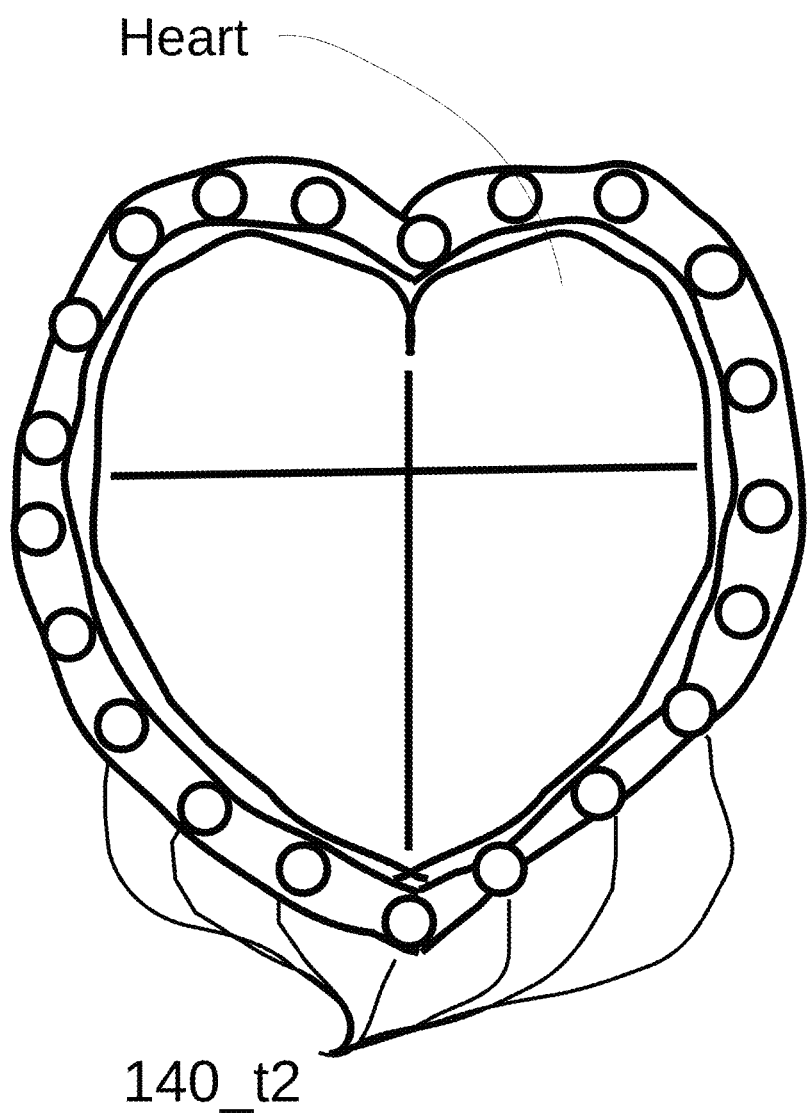

FIG. 4—Passive electrodes, supercapacitor-type, distributed on a membrane surrounding the pericardio. Such a membrane was developed, fabricated and actually used on a rabbit's heart ex-vivo (see references below). In this case the membrane around the pericardium was populated with data collecting sensors, as pressure sensors, electrical reading electrodes, pH sensors, etc., and they took the heart out of the unfortunate rabbit, then kept it beating with a heart pacemaker and a heart-lung machine. Our device would have passive electrodes on the membrane instead, so it is a simple modification of an existing technology.

FIG. 5A—Electric fields below the skin on a TENS device.

FIG. 5B—Electric fields below the skin on a TENS device.

Figure 6:
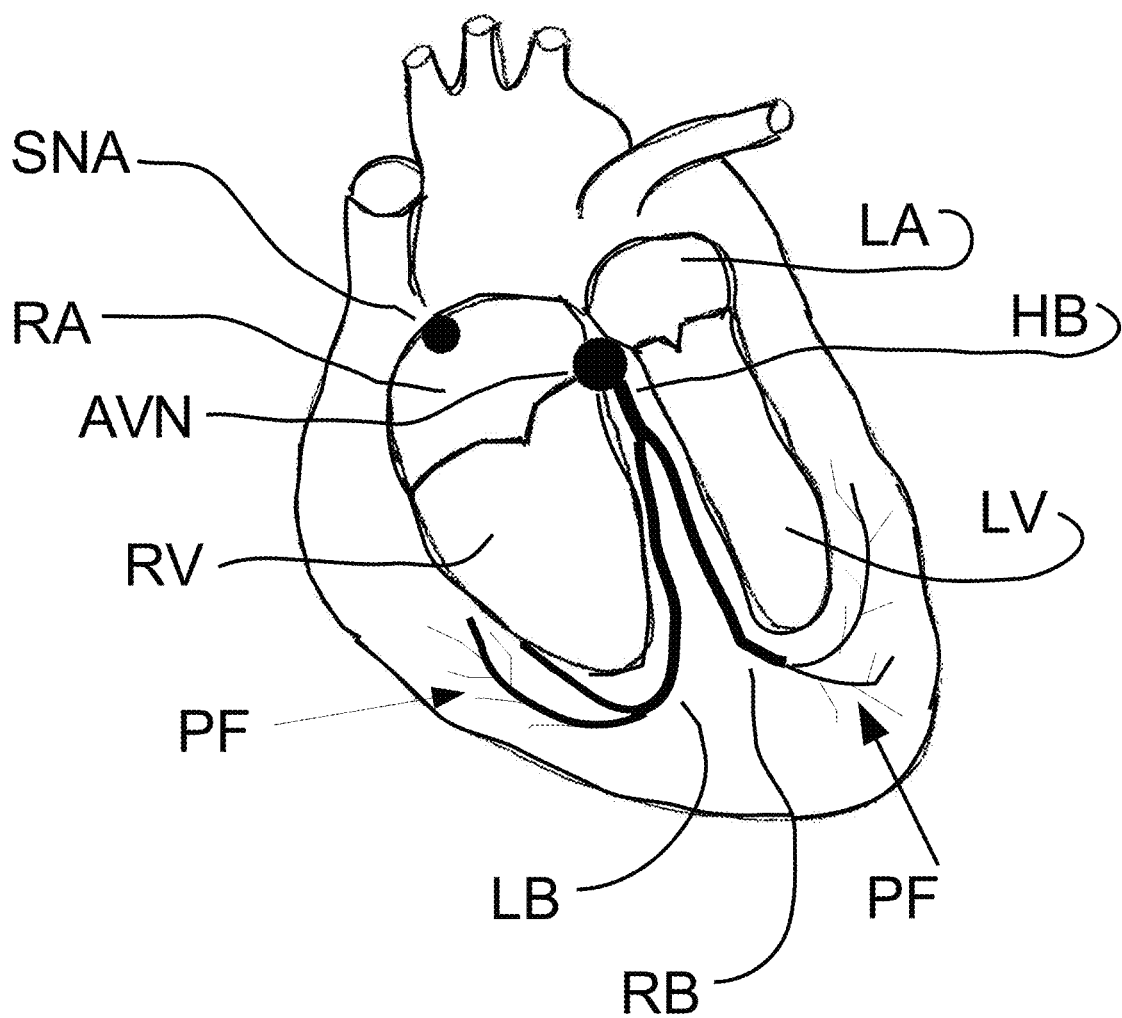

FIG. 6—A heart with its parts.

FIG. 7A—Part of a contraction sequence of an atrium, or upper part of the heart.

FIG. 7B—Part of a contraction sequence of an atrium, or upper part of the heart.

FIG. 7C—Part of a contraction sequence of an atrium, or upper part of the heart.

FIG. 7D—Part of a contraction sequence of an atrium, or upper part of the heart.

Figure 8A:
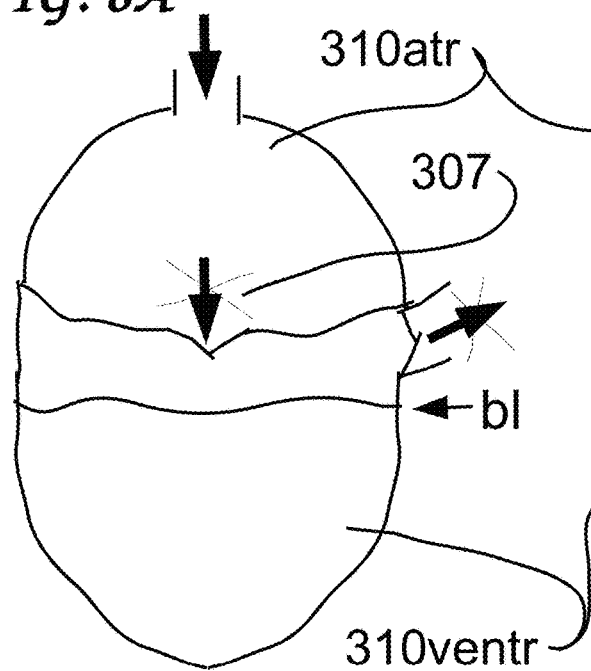

FIG. 8A—Part of a contraction sequence of a ventricle, or lower part of the heart.

Figure 8B:
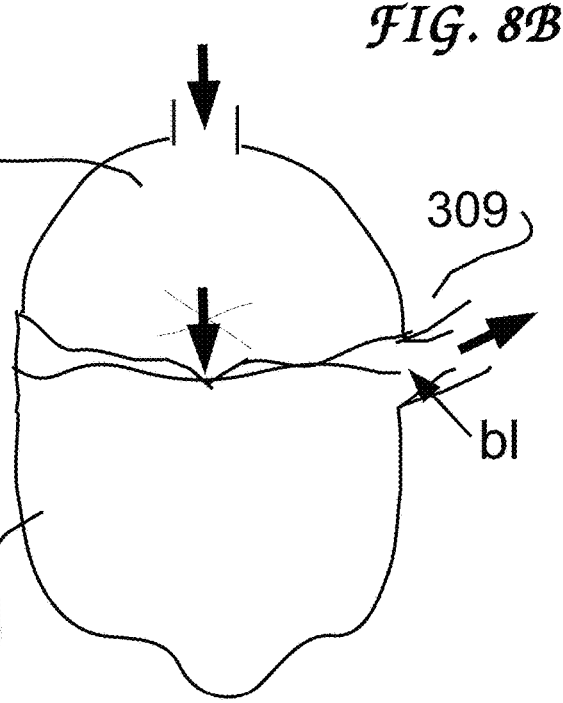

FIG. 8B—Part of a contraction sequence of a ventricle, or lower part of the heart.

Figure 8C:
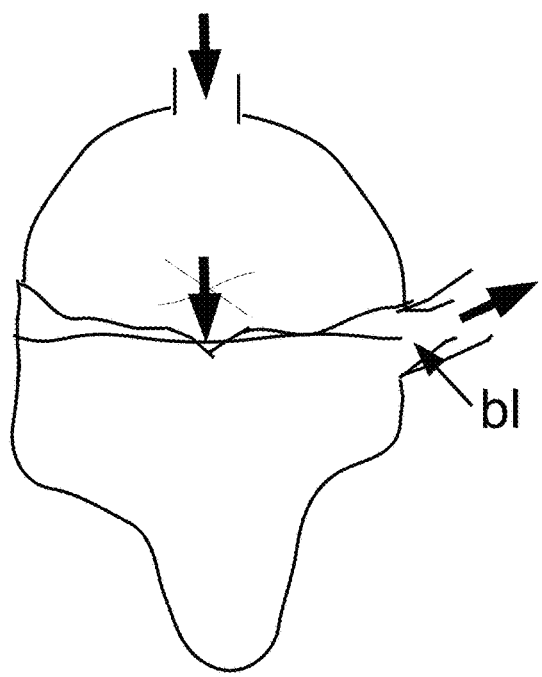

FIG. 8C—Part of a contraction sequence of a ventricle, or lower part of the heart.

Figure 8D:
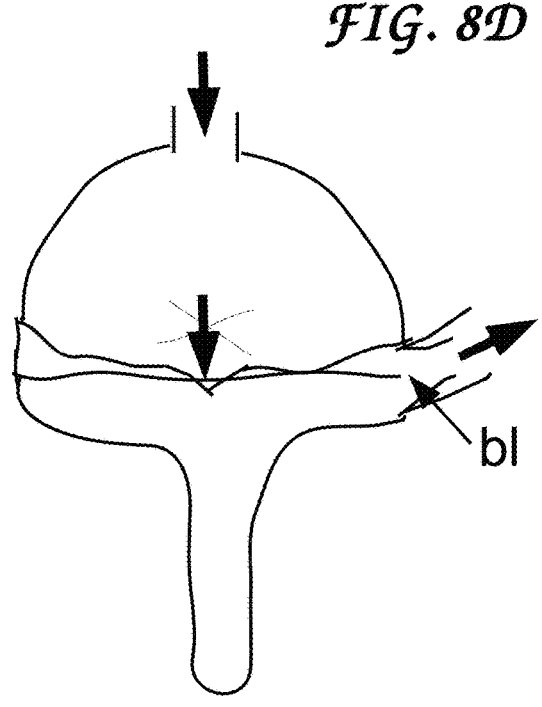

FIG. 8D—Part of a contraction sequence of a ventricle, or lower part of the heart.

Figure 9:
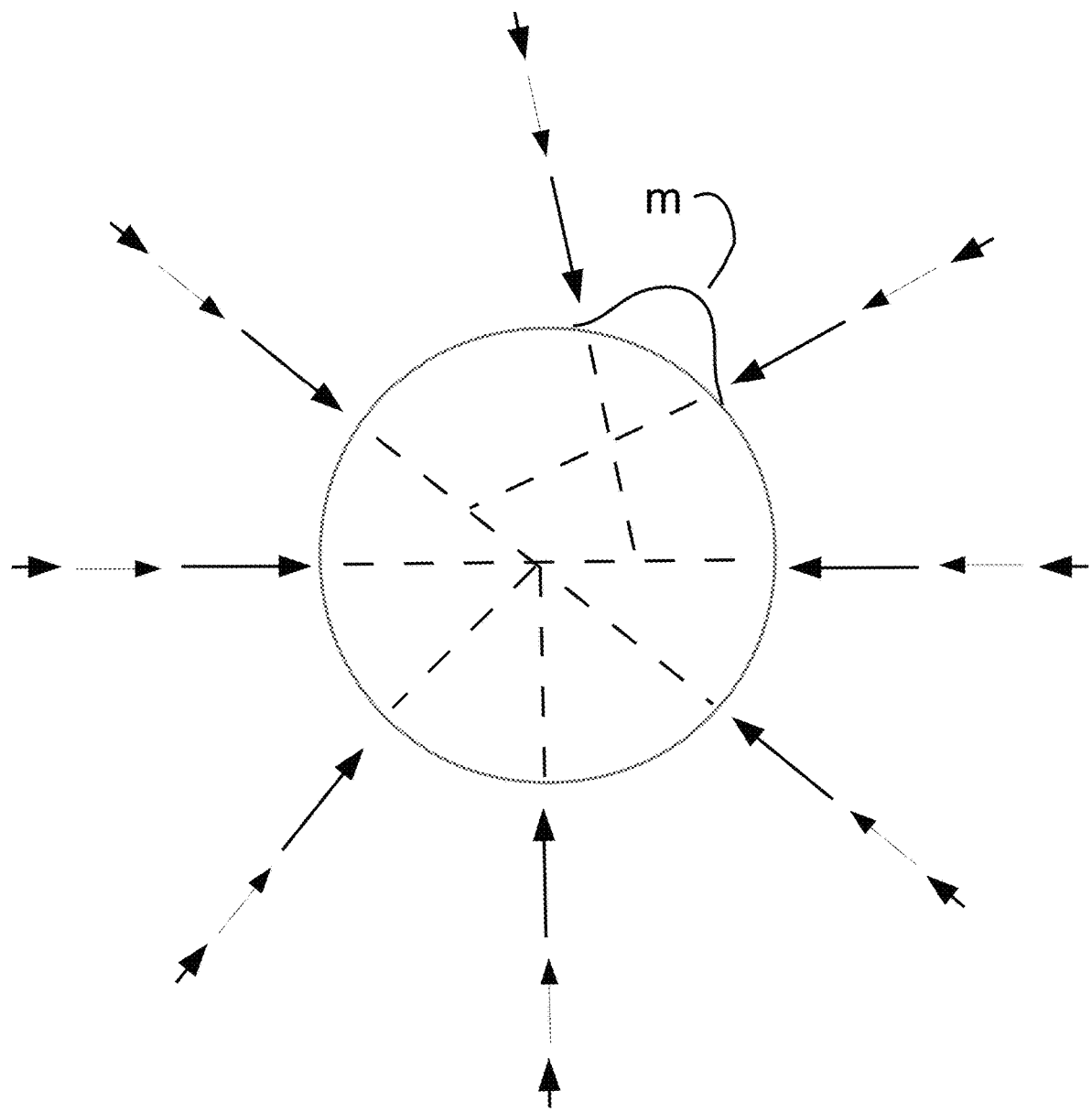

FIG. 9—Gravitational field of the earth with a mountain causing a deviation on the otherwise gravitational field toward the geometrical center of the planet.

Figure 10A:
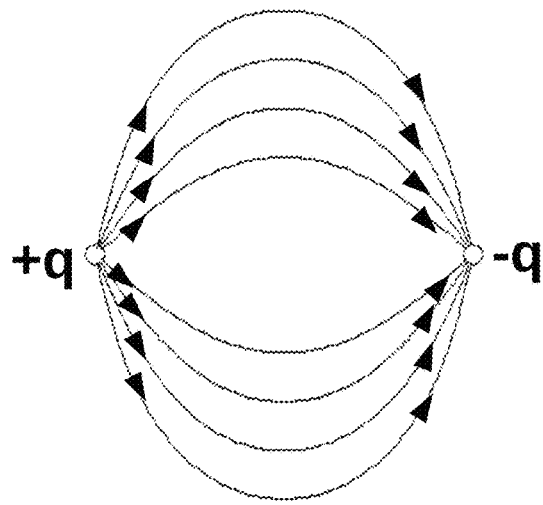

FIG. 10A—Electric field of a combination of electric charges.

Figure 10B:
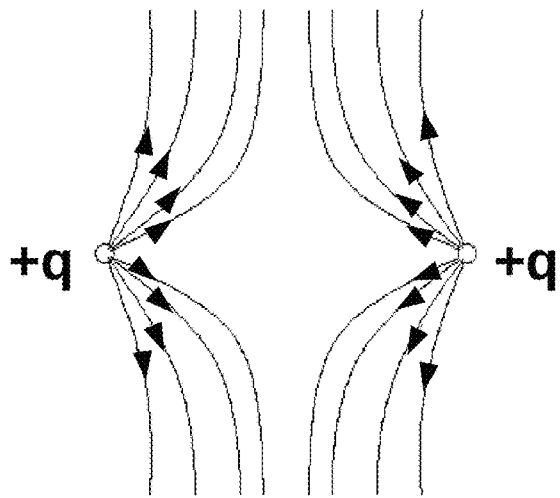

FIG. 10B—Electric field of a combination of electric charges.

Figure 10C:
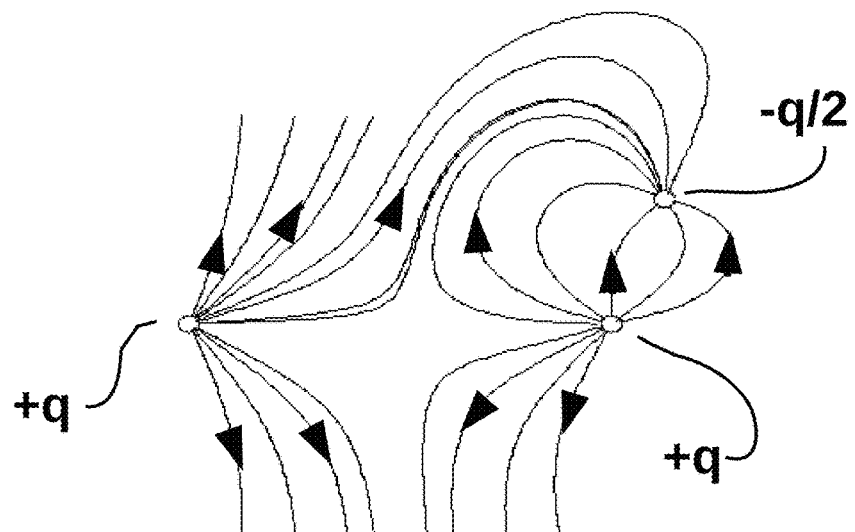

FIG. 10C—Electric field of a combination of electric charges.

Figure 10D:
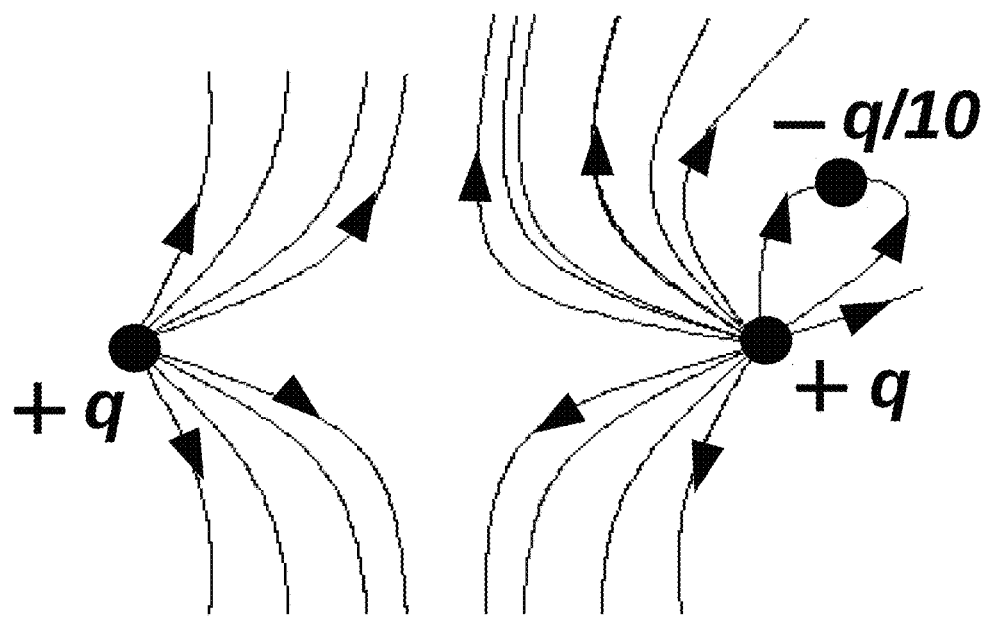

FIG. 10D—Electric field of a combination of electric charges.

Figure 10E:
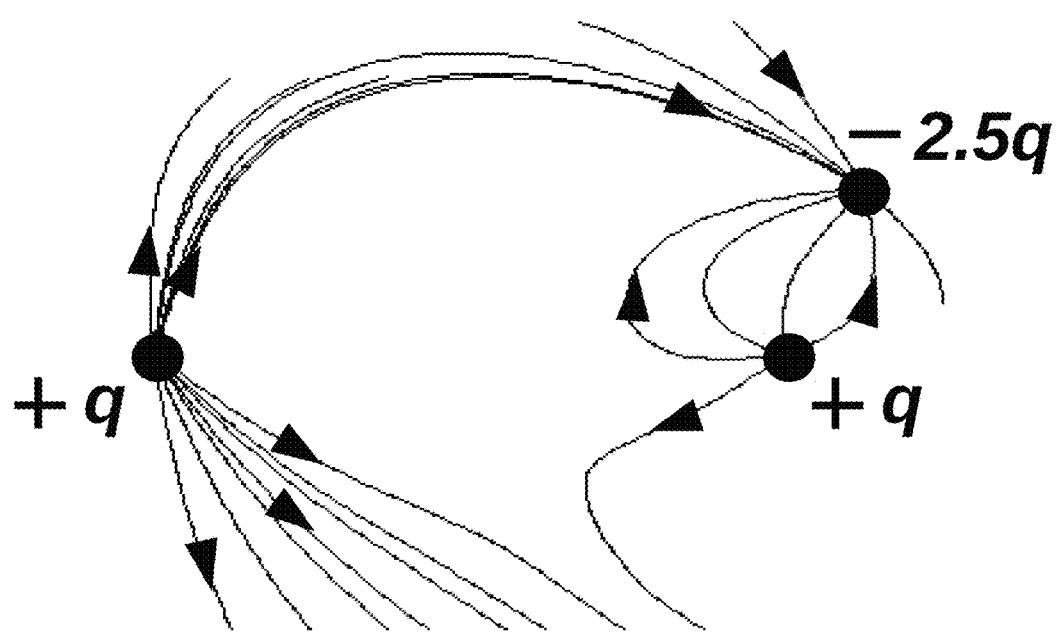

FIG. 10E—Electric field of a combination of electric charges.

Figure 11:
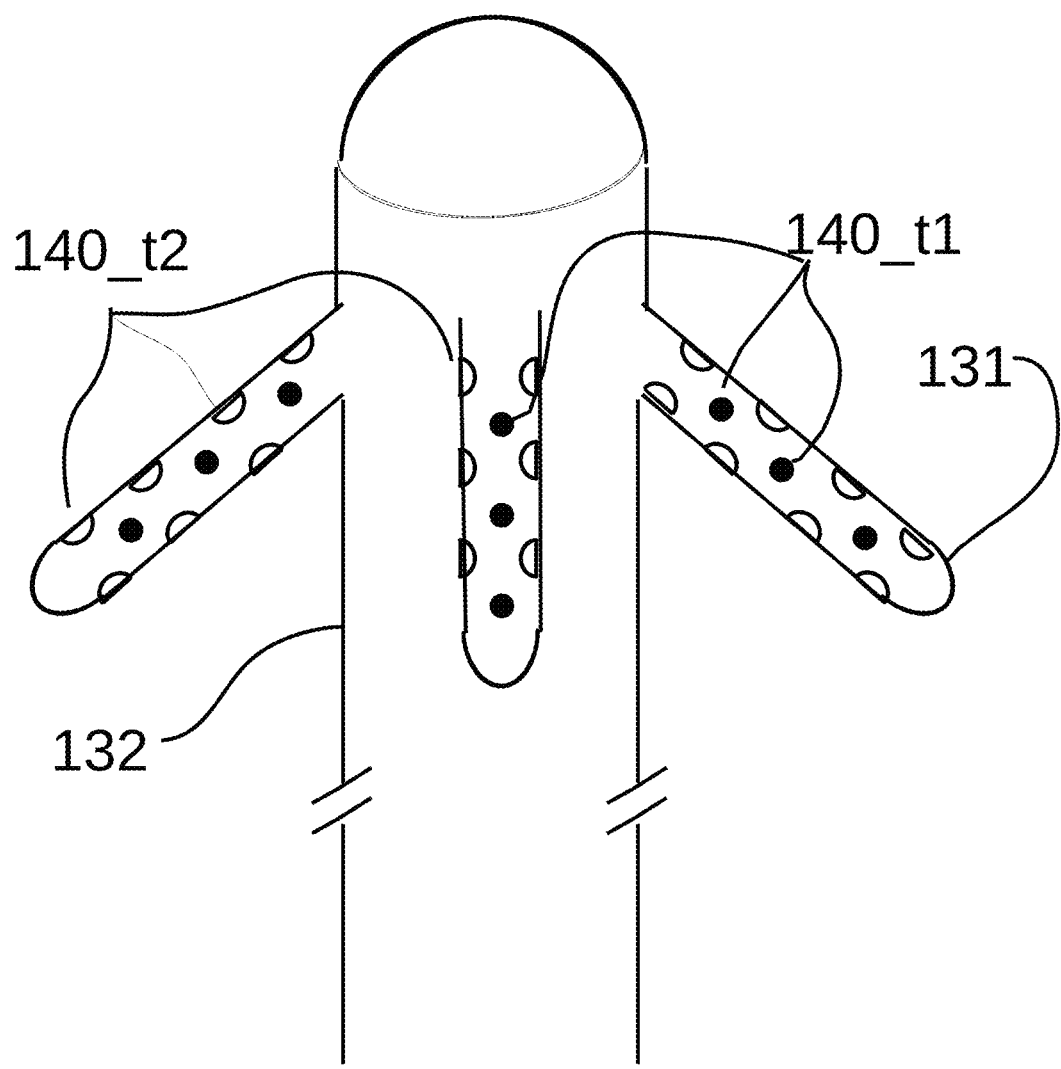

FIG. 11—A heart electric stimulator with electrodes.

Figure 12A:
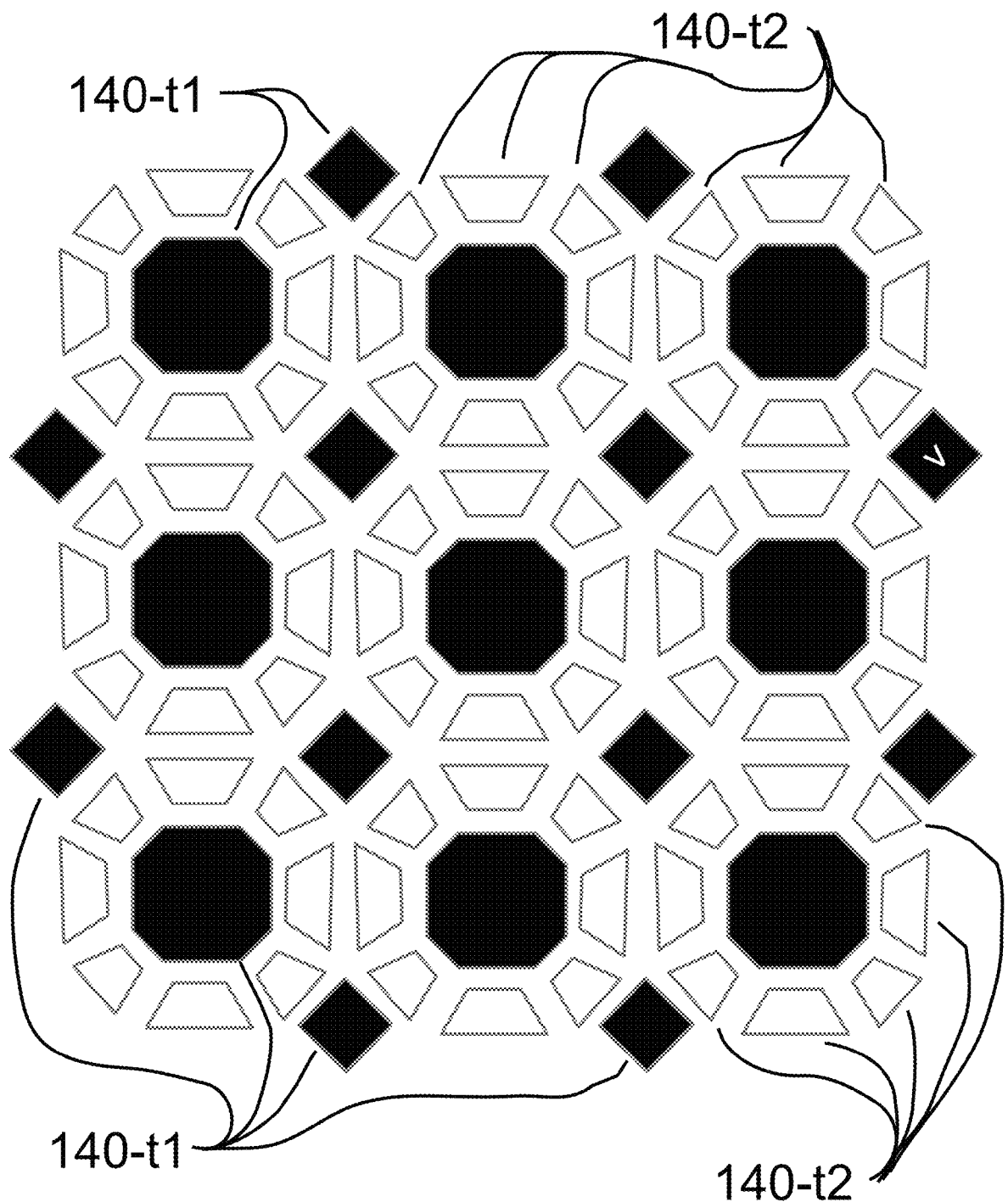

FIG. 12A—Possible types of electrodes.

Figure 12B:
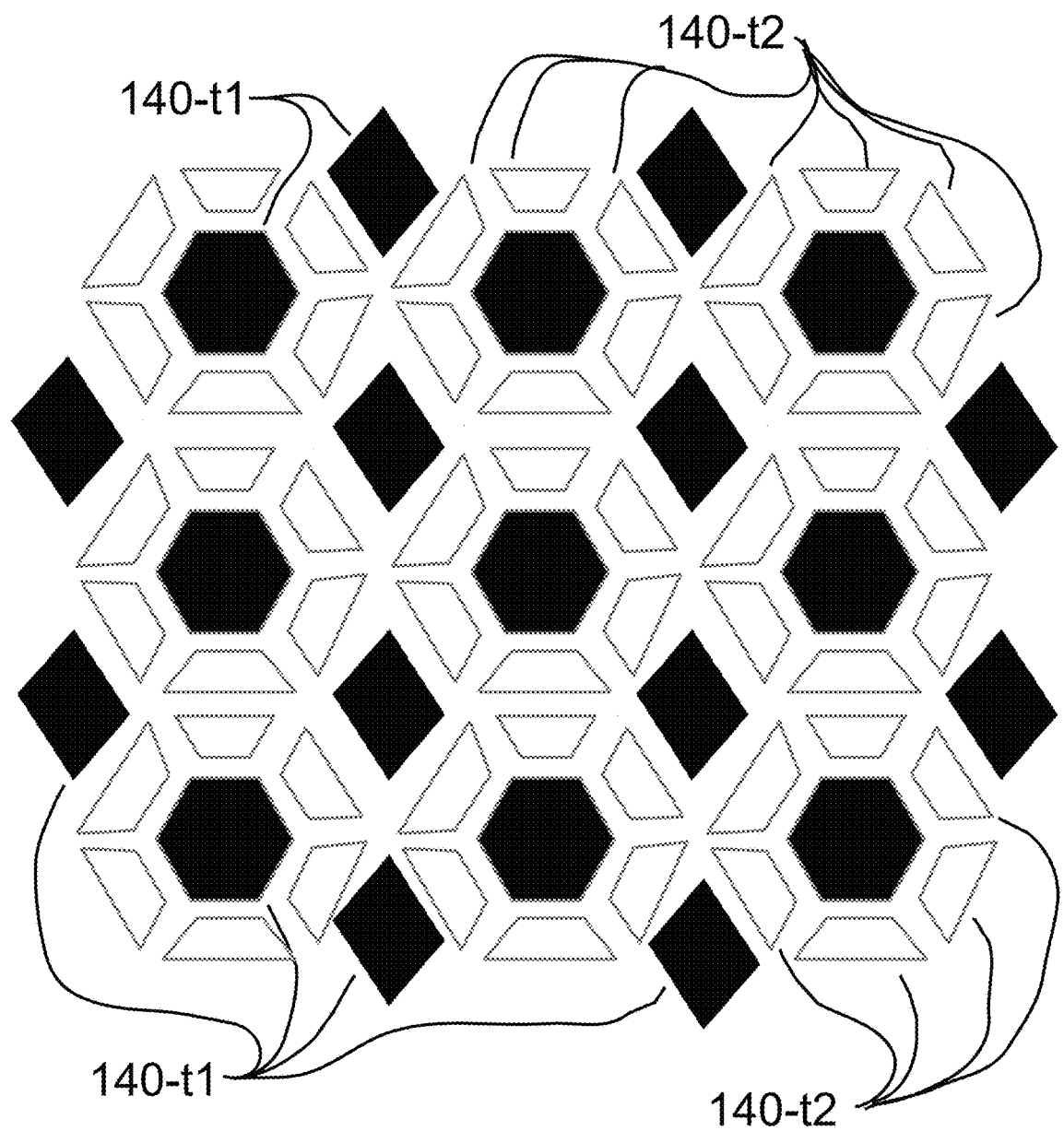

FIG. 12B—Possible types of electrodes.

Figure 13:
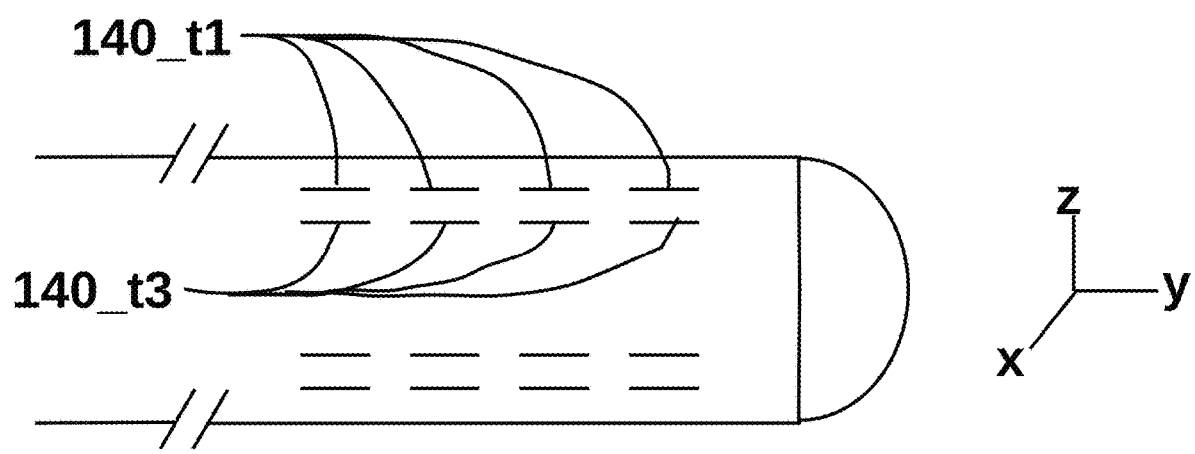

FIG. 13—Subterranean type of electrode $140\_t3$.

LIST OF REFERENCE NUMERALS

BAT1=Battery and controlling electronics box, usually implanted in the patient's chest.

MP1=Microprocessor 1. One of the possible units capable of executing a programmable sequence of instructions, as the venerable 8085, or the 8086 (which was the brain of the first IBM-PC), 80286, 80386, 80487, pentium, DSP, microcontrollers, etc. Some of these may include memory, DAC, ADC, and interface devices.

100=body of picafina of our invention.

110=electrical energy storage unit (e.g., a battery)+microprocessor (MP1)+parallel-to-serial converter.

122=Serial address (may also include return ground, or may use the same return/ground as power 124).

123=reset line/control bits.

124=power conveying means.

130=ST1=electrical stimulating probe, in the main embodiment is screwed in the inner part of the heart, brain, or other organs.

131=anchoring arms to prevent the heart stimulator type (piquita) from moving back once it is forced into the endocardio/miocardio.

132=main body of piquita heart pacemaker.

140-$t1$=type1 or active electrodes (standard electrodes, capable of injecting current in its neighborhood).

140-$t2$=type2 or field shaping electrodes (electrically insulated electrodes, capable of influencing the electric field lines, but not capable to inject current). Typically type 2, field shaping electrodes are covered by a silicon dioxide layer, but any other insulator is possible, the type of insulator being not important for our invention.

210=memory with local address for each electrode 140.

220=SW=switch to turn electrodes on/off.

230=comparator to determine if switch 220 should be turned on or off.

240=digital comparator/decoder.

250=enable bit for 260.

260=comparator/decoder for stimulator addresses.

307=tricuspid valve, between the right atrium and ventricle.

309=pulmonary valve, exit from the right ventricle.

310$atr$=atrium.

310$ventr$=ventricle.

410=hermetically sealed box containing the energy storage unit (battery), the microprocessor MP1, the serial-to-parallel converter and all the necessary electronics for the device to operate, as is used in prior art.

510=serial-to-parallel converter.

520=parallel lines for addresses (may also be used for control and data).

830=address decoders (AddDec) alphabetical labels

A=digital, binary address lines.

AVN=Atrial-ventricular node.

B=power line (voltage or current source).

bl=blood level.

HB=His Bundle.

LBB=Left bundle branch.

LA=Left atrium.

LV=Left ventricle.

m=mountain (exaggerated height for display)

PF=Purkinje fibers.

RA=right atrium.

RBB=Right bundle brunch.

RV=Right ventricle.

SNA=sino-atrial node.

SW=also 220 and 810.

DETAILED DESCRIPTION

Overview

The main embodiment of our invention is one of the dental tools ordinarily used by the dentists to inflict pain on their clients, as the Jacquette Scaler U15/30, the Sickle Scaler H6/H7, the Probe #9, the Explorer #23, the Explorer #23/17A, the Tartar Remover Scaler, the Root Canal Spreaders 25-D11, the Margin Trimmer (Distal and Mesial), the Gracey Periodontal Curettes, the Periodontal Probe, the Heidman Spatula and many others. These may or may not be used together with a variation of a TENS supporting electrodes, preferably a multiplicity of electrodes attached to a malleable surface which may, for example, be temporarily fixed to the outer skin or the patient, most likely at the cheek. Note that it is possible to apply our invention without the TENS supporting electrodes. Other dental tools are also good means to apply our invention, as any of the drills used by the dentist to remove dental tissue attacked by the cavity-causing bacteria, or the tools used to extract the nerve during the dreaded procedure known as root canal treatment. All of these share a common trait of being made of metals or some other electric conductive materials and able to carry electric current to their tips, which current is then injected onto the mouth of the patient exactly at the point where the pain is being inflicted on the patient by the very tool that is injecting the pain-suppressing electric current.

The main embodiment of our invention is seen at FIGS. 1A, 1B and 1C. These figures show several variations of a malleable sheet-like supporting structure Pat with one or more electrodes that may be or either type (active electrodes of field shaping electrodes, 140_t1 and 140_t2, respectively) or both types. For example, the main embodiment may have a malleable sheet-like supporting structure Pat with one active electrode 140_t1 (see figure FIG. 1A), or a malleable sheet-like supporting structure Pat with one field shaping electrode 140_t2, or a malleable sheet-like supporting structure Pat with one of each type 140_t1 and 140_t2, or any other combination (FIGS. 1B and 1C). The malleable sheet-like supporting structure Pat can be made of any material that is reasonably malleable, similar to a bed sheet, as cotton, wool, silk, small metal wires, nylon, thin metal foil, rubber or rubberized materials, plastics, etc. or any other that is capable of adapting its own shape to a curved surface, on which the malleable sheet-like supporting structure Pat is applied. The malleable sheet-like supporting structure Pat may have some type of attaching device to cause it to be in fixed position with the object on which it is applied, for example a glue, a zipper, velcro, a set of screws, stitches, rubber bands and gaskets, or any other device capable of keeping the malleable sheet-like supporting structure Pat in place, or moving within a certain limit that depends on the case. The electrodes may be any material, as metal, metalized foil, or any electrically conducting material. The electrodes may be a simple material or they may be constructed with the technology used to manufacture supercapacitors, which produces a large number of interconnected holes into the bulk of the material, which is capable of increasing the surface of the electrode by a factor of 1,000 and much more, which in turn increases the electrode's capacitance and with it increases the charge delivering ability of the electrode (important for active electrodes 140_t1) and also the field strength created by the electrode (important for the field shaping electrodes 140_t2).

Examples of the main embodiment are variations or extensions, or improvements on the existing TENS devices, which then may have a general external appearance of the old, traditional TENS patch but have the new field shaping electrodes 140_t2, or membranes to cover the heart, as described by LizhiXu, Igor R. Efimov et al. "3D multifunctional integumentary membranes for spatiotemporal cardiac measurements and stimulation across the entire epicardium" Nature Comm Vol 5 Pg 3329 (March 2014), Colleen Clancy and Yang Xiang "Wrapped around the heart" Nature Vol 507 pg 43 (6 Mar. 2014), Pierre Martin "Une membrane artificielle pour surveiller le coeur" La Recherche (1 Mai 2014). The invention is not limited to these two applications or to these two shapes or these two sizes, but is applicable to any other situation which uses electrical stimulation.

FIG. 2 shows one of the applications of the main embodiment of our invention, which we call Dirichlet's shirt, and which is for heart pacemaking applications. Here one see passive electrodes distributed on a wearable shirt-like support. Such external passive electrodes offer the advantage of using external batteries, simplifying the problem of electrical energy for the electrodes. The fractional surface coverage could be of the order of 75%, which is the approximate solid angle coverage offered by the shirt's front+back+sides. Appropriate modifications that adapt what is described in the main embodiment for other organs, as the brain, nerves in general, the stomach, etc. are obvious for persons that work in the field of electrical stimulation and have knowledge of electrostatic and electromagnetic theories. For example, for brain use, the Dirichlet's shirt would be a kind of a hat, a Dirichlet's hat, which may have also extensions behind the head, as used for extra sun protection, and extensions over the ears, as used in cold winters for extra protection against the cold, and perhaps other new surfaces surrounding the head as possible to use, all with view of providing as large a surface as possible around the desired area of influence. For stomach, intestines, etc, it would be a kind of a belt, the Dirichlet's belt, similar to the wide belt used by workers that need to lift loads all the time, as warehouse workers, household movers, etc. usually 20 cm wide. The Dirichlet's belt could be wider than the belts used by workers to protect against hernias, both in front and back, due to their intended function.

FIG. 3 shows a variation of our invention with some connecting wires. The Dirichlet shirt of our invention has wires 124 as seen if FIG. 3 extending from the controlling electronics, microprocessor and battery to each electrode 140 (of either type, t1 or t2). Wires 124 may be either standard wires or may also be printed circuit wires, as in printed circuit boards. The technology of printed circuits is a well advanced technology with many methods to print the wires, and the wire manufacturing is not part of this invention, as any of the existing technologies are acceptable to implement the invention.

The main embodiment uses 10 wires from the battery pack/control unit 110 to the Dirichlet shirt, which are connected to the 10 available electrodes 140 by the 10 wires 124—one wire for each electrode 140. This particular choice of 10 wires and 10 electrodes should not be taken as a limitation on the invention, because more wires and electrodes, or less wires and electrodes are possible still within the scope of the invention, as obvious to people familiar with the art of electronics. It is also possible to connect the ground (or return) wire to any number of electrodes (or pads), both type-1 and type-2. It is also possible to use the wires as address bits, in which case 10 wires would be able to select for 2**10=1024 different electrodes.

As seen in FIG. 2, the main embodiment consists of a modified ordinary shirt, for example, a T-shirt or a V-neck type, preferably either tight on the body or conforming to the body, on which there exists a multiplicity of field shaping electrodes (also known as type 2 electrodes), preferably with the necessary battery and electronics together as a unit, but the battery and electronics may be separate from the shirt too, without changing the nature of the invention. The Dirichlet's shirt may be, for example, a modified T-shirt, preferably fit on the wearer (that is, tight without squeezing the wearer), with a multiplicity of pockets as shown in FIG. 2 which are so designed as to hold specially designed electrodes both of the field shaping and active type, and one or more extra similar pockets capable of holding an electric cell or battery and the associated controlling electronics, which may be in the same box. The pockets for the electrodes are so designed that they allow the field shaping electrodes to work for their objective, which means that typically the electrodes, when inserted in their pockets, should have a flat surface facing the body of the person wearing the Dirichlet's shirt. The electrodes, which may be of the field shaping electrode type only but may also be of both the field shaping variety and the active or current injecting type in the main embodiment, and the field shaping electrode may be made with the supercapacitor technology, with a porous very large surface area, or may be simple flat surfaces. The Dirichlet shirt may have electrodes on all its surface and the electrodes are preferably facing the skin of the wearer, that is, the electrodes are preferably at the inner surface of the Dirichlet shirt, preferably in direct contact with the skin. Our Dirichlet's shirt is adaptable to be worn as an ordinary even fashionable shirt as any polka dot shirt that becomes fashionable for women from time to time.

FIG. 4 shows an improvement over the Dirichlet's shirt. FIG. 4 is a membrane covering the heart with electrodes on its surface. FIG. 4 shows type 2 (field shaping electrodes) only, but it usually would have both type 1 and type 2 electrodes. The hardware shown in FIG. 4 has been developed recently and has been published in Nature, in La Recherce, and other publications. It was developed to make measurements on the heart, fitted with all sorts of sensors, but not with the field shaping electrode of our invention. See references LizhiXu (2014), Clancy (2014) and Martin (2014). The reader is encouraged to go see the pictures of these membranes. Our invention described here is not new in the membrane, it is new on the use of the passive electrodes on these membranes.

To physically achieve the above description, the controlling mechanism, in this case a microcontroller residing in the battery/control unit 110 (FIG. 3), is loaded with a program (or software), which is capable of executing automatic repetitive tasks following a programmed sequence the details of which are adjusted by a medical professional or by the patient himself, which determines a particular combination of active and field shaping electrodes to use, also able to determine which electrodes of each type to use, also able to send this information by wires to the stimulating unit 130. The correct sequence can be determined, for example, by the examination of an EKG (Electro Cardiogram) while varying the active electrodes of each type, their voltages and relative time sequence, if the electrical stimulation is acting on the heart, or the correct sequence can be determined by observing the muscle contraction sequence if the stimulation is a TENS stimulation used by a chiropractor or by a physical therapist to treat some muscle or some tendon problem, etc., depending on the case. The microprocessor, located in box 110, select which wires 124 to be connected to electric power and the voltage level as well, which may be different at each wire 124. Each were 124 connects to one of the electrodes 14041 or 140-$t2$. Each electrode type can be turned on or off (connected or disconnected from the electrical power) under the control of microprocessor.

The random placement, shape and size of the electrodes is a distinct feature of our invention, as it contributes for the creation of a spatial asymmetry of the electrodes, which in turn causes an asymmetry in the spatial distribution of both the electric field E and of the injected current i, either its magnitude or its direction. Careful selection of which electrodes to turn on, and at which electric potentials (voltages) can create the most desirable electric field shape E (x) on the volume of the heart. A careful selection of which electrodes is able to produce a better resulting stimulation which is suited to the asymmetric heart muscle 3-dimensional shape and causes a more complete squeezing sequence and better ejection fraction (the fraction of blood sent out of the heart). It is to be noted that if any symmetry is required, our invention is backwards compatible, being able to reproduce heart pacemakers stimulating surfaces as a particular case of an arbitrary shaped surface. Note that if a symmetry of current magnitude and direction is desired, it can still be achieved within a reasonable accuracy, by the appropriate selection of a number of electrodes which, as a set, defines the desired symmetry. Naturally the degree of symmetry possible to be achieved depends on the number of electrodes available: more asymmetry with more electrodes (that is, more complex electric fields with more electrodes).

Operation of Invention

Background Information on Operation of the Invention.

The operation of our invention is based on the effect of electric fields on electric charges, and on the Newtonian theories relating forces, masses and acceleration, all of which is part of most introductory physics courses. To understand the operation of our invention we will use two examples: the case of TENS and the case of the heart, but the same principles apply to other applications.

FIGS. 5A and 5B show the skin of a person, with the flesh below the skin line, out of the body above the skin line. For simplicity the TENS is not completely shown, but only one active electrode 140_$t1$ and four field-shaping electrodes 140_$t2$, as indicated. Also, to avoid cluttering the drawing only two of the field shaping electrodes are marked, the electrodes on the right of the figure, the other two field shaping electrodes at the left being without indicative letters but only known to be field shaping electrodes of the type 140_$t2$ for being drawn as open rectangles. FIG. 5A shows the forces for a charge q on the field shaping electrodes 140_$t2$, while 5B shows the forces for a charge 2q (twice as large) on the field shaping electrodes 140_$t2$. It worth to point out here that the larger charge on the electrodes are a consequence of a larger electric potential (or larger voltage as the Americans say it), and we use the language of the charges here because it is closer to the physical principles and also direct consequences of Coulomb's law that are known as a function of the electric charges and not as a function of the electric potentials. The forces on a charge at the same location below the skin are shown: four forces (at an oblique angle) due to each of the four field shaping electrodes 140_$t2$ and the resultant force (or total force, or combined force) that in this case happens to be on the vertical direction down, a result that can be seen without calculations if one considers the symmetry of the problem. As it is seen on the figures, the force on the case of larger electric charges is larger, and consequently the speed of the charges injected by the central active electrode 140_$t1$ is larger and the charges will also penetrate deeper into the tissue of the patient on the second, lower case than on the first, upper case. So, FIGS. 5A and 5B show the effect of the field shaping electrodes 140_$t2$: they control the location of the electric currents injected in the body by the active electrodes 140_$t1$, which are the only electrodes used by the existing devices.

The second example we use to show the operation of our invention is the heart. The reader must keep in mind what causes the heart to contract, and therefore to pump the blood, and the sequential nature of this contraction as well, which is the propagation of the ions through the heart muscles. In fact this is also true for the motion of my fingers as I type these very words that the reader is reading right now: similarly to the heart contraction, my fingers move due to the arrival of electric charges (ions) that are transmitted by the nerves, according to a sequence that started at my crazy brain—it is all the same thing, the heart and my fingers. FIG. 6 displays a human heart with the main parts indicated in it. Left and right are designations from the point of view of the person in which the heart is, which is the opposite of the viewer, facing the person. The right and left sections are responsible for two independent closed cycle blood flow: the right side of the heart pumps blood to the lungs then back, so it is called the pulmonary circulation, while the left side of the heart pumps blood to the whole body.

The heart muscle contraction occurs as a consequence of and following the propagating electric pulse that moves in 3-D (three dimensions) through the heart muscle from an initiating point (the sino-atrial node), which is located at the top of the right atrium—the 3-D electric pulse propagation through the heart muscle is important for the operation of our invention, as it will be seen in the sequel. This propagating electric pulse is known by the medical people as a depolarization wave, and the medical people associate a depolarization event to a muscle contraction event. This sequential contraction, characteristic of all peristaltic pumps, is similar to the process of squeezing toothpaste out of the tube: it is a progressive squeezing sequence which progress from the back (or entrance) to the to the forward (or exit) port. This progressive contraction is in contradistinction with a simultaneous contraction from all sides, as happen when an air balloon pops or when a person squeezes a tennis ball to exercise the muscles at the arm—the few people that do exercise! The collapsing popping air balloon is under the influence of a mostly isotropic force created by the air pressure, which is virtually the same on all the surface of the balloon, which causes that it collapse isotropically, as a sphere of progressing smaller radius. For the toothpaste case, virtually most minimally intelligent person squeezes the tube starting from the back and progressing forward as more squeezing is needed. Granted that there are people that extract the toothpaste squeezing the tube from the middle, but it is universally acknowledged to be inefficient to do so, even by the very people that do it; they make a huge mess and drive other family members crazy trying to fix it all the time. The most perfect simultaneous contraction from all sides is the plutonium bomb, a situation in which great care is taken so that the inward pressure wave causes a perfectly symmetric contraction of the plutonium core. If the core contraction is not perfectly symmetric, the core squeezes out through the point of smaller pressure and the bomb does not explode, a result that would be much preferable but regrettably is not the result acceptable by the bombers. The heart squeezes as a properly used toothpaste tube, not as a collapsing air balloon that collapses upon itself from all directions at the same time, not as an exercising squeezing tennis ball, and not, which is the utmost example of a body squeezing down perfectly symmetrically from all directions, a plutonium bomb. Yet, the heart is not as good as it should be at squeezing from entrance to exit, and our invention improves the heart, directing it to go into a properly sequential squeezing. Pondering at the imperfect heart squeezing sequence it may be said that the American intelligent creator was not that intelligent after all!

One of the reasons for the lack of appreciation of this sequential contraction is that it is not perfect, as if it occurred within a well-engineered pump. Moreover, the heart is more or less hanging inside the upper torso, suspended by the blood vessels and somewhat resting on the diaphragm, as opposed to a proper peristaltic pump, fixed in relation to the machine in which it works. As a consequence of this, the heart twists and moves on all directions as it pumps, masking its sequential motion. Then, each half squeezes in ½ second, too short a time for a human being to perceive in detail. Finally, it is the opinion of the inventor that the MDs are not interested in the reasons of things, which unfortunately causes them to miss the solution to the problems their patients face.

This sequential contraction is valid for all four heart chambers: the right atrium, which has its entrance at the top and exit at the bottom, contains the initiating electrical cells at its top (the sino-atrial node), from which the electrical pulse propagates in its muscle walls from top to bottom, which is, accordingly, the sequential squeezing, as per FIGS. 7A, 7B, 7C and 7D (the figure exaggerates and distorts the situation for display purposes and because the inventor is unskilled in drawing too). The ventricle, on the other hand, has both entrance and exit ports at its top, which poses a difficult problem to solve, needing as it does, to contract from bottom to top, to force the blood to exit at the top, while the electric pulse is coming from the top! This was solved by the intelligent designer with a mechanism to arrest the electric pulse at the bottom of the atrium (else the ventricle would contract from top to bottom, where there is no exit point for the blood!), and another specialized set of cells, the atrium-ventricular node, which, upon receiving the weak electric signal that is coming down from the sino-atrial node, re-start another electric pulse, but with a few milliseconds delay, which is in turn delivered for propagation through a set of specialized fast propagating cells lining the wall between the two ventricles: the His short bundle, followed by the right and left bundles, and finally the Purkinje fibers that spread the electrical pulse throughout the bottom and sides of both ventricles. This second electric pulse, delayed from the initial pulse from the sino-atrial node, is then injected at the bottom of the ventricles, from where it propagates upwards, causing an upwards sequential contraction (in the opposite direction as the initial atrium contraction!), as required by an exit point at its top. This process of upwards contraction of the ventricle, the lower chamber, is displayed in FIGS. 8A, 8B, 8C and 8D. It works, though any respectable engineer would have made a different design, with a ventricular exit at the bottom, not at the top, therefore eliminating the His bundle, the left and right bundle and the Purkinjie fibers, which is a source of many hearts malfunctions. As any respectable engineer knows, unnecessary parts should be avoided if possible, and the bundles and the Purkinjie fibers can be made unnecessary with a better design of the heart. Looking at the heart poor design at least one can take solace in that this is not the worse design error of the human body—one just has to look at the brain. The left heart pumping in essentially the same, varying only in minor details, there is no need to repeat.

This said, the reader should keep in mind two important points here which is the detail on which the whole invention hinges, and which we urge the reader to pay attention and ponder on. First, that not only is the heart contraction caused by an electric pulse but also that this electrical pulse, because it relies on the propagation of heavy positive ions in a viscous medium, it propagates relatively slowly through its muscles and special fibers. The propagation of this electrical pulse is very slow as far as electric events happens, the whole process taking just below one second to complete (at a normal heart beating rate of 70 beats per minute). This means that the times involved are of the order of tens and even hundreds of milliseconds. This slow propagation time is important for our invention to work, as it will become evident in the sequel. The much faster propagation of electric charges in wires and transistors (1 million times faster), allows that a human-engineered circuit can take over the natural process and improve on it—a very interesting project indeed, just think of it!

In this main embodiment, the variation and improvement over our previous cited patents is that there are two types of electrodes (conductive and insulated electrodes, also called active and field shaping electrodes, also called type-1 and type-2 electrodes), which may also be of several shapes and sizes and possibly randomly located on the surface of the device, while still attempting to cover most of the surface with electrodes. The possible random arrangement of the electrodes functions to break the space symmetry, therefore allowing better control of the injected current, which may need to be asymmetric—most likely will need to be asymmetric, following the heart shape, which is asymmetric. It is to be recalled here that no asymmetric electric field lines can be achieved using a symmetric electrode array, and further, that the resulting electric field shape necessarily have the same symmetry than the symmetry of the surface shape that produces it.

The shape and size differences is not necessary for the main embodiment, which would also work with electrodes (and non-conductive field shaping surfaces) of the same shape and/or size. The invention is the same for simpler electrode arrays which may be simpler and less expensive to produce, such a choice being a matter of production/cost compromise, still under the scope of the main embodiment. For example, it is possible to control the vector injected electric current (magnitude and direction) with circular electrodes (of either type, conductive or current injecting and insulated or field shaping electrodes) that are of different sizes and randomly distributed on the surface of the Dirichlet shirt. It is also possible to control the vector injected electric current with circular electrodes (of either type), that are of the same size and randomly distributed on the surface of the Dirichlet shirt, in this more restrictive case, same shape and size but randomly distributed on the supporting surface. Or it is also possible to control the injected electric current vector with circular electrodes that are of the same shape and size and orderly distributed on the surface of the Dirichlet shirt, this being the most symmetric electrode arrangement of all. The difference between these options is simply the degree of possible variations and fine control on the vector current, and the choice between each option is based on a cost/benefit analysis, all being still within the scope of our invention. It may also be the case that the shape, size and location of the electrodes be dictated by fashion if the electrodes are visible, which depends on the technology used.

A moment of thought will show the reader that the good operation of the heart depends on the correct propagation of the electric current through the heart muscle. This latter depends on the electrical characteristics of the diverse muscles (cells) which comprise the heart, including rapidly electric propagating cells (His fibers, left and right bundles, the Purkinjie cells and more), endocardio and miocardio cells, all of which suffer individual variations from person to person, due to their genetic make-up, to which other variations accumulate during the person's lifetime, due to his exercise and eating habits, etc, to which unlucky events as small localized infarctions and heart breaking events add scar tissues with different conductivity than health cells, which then causes loss of contraction capability, all adding to a conceptually simple problem, yet of complex analytical solution due to the large numbers of factors involved. This, in turn, is the problem which our invention address: how to better adjust the 3-D electric current propagation through the heart, in order to cause the best heart squeezing sequence possible for a particular individual, given his possibilities as determined by the physical conditions of his heart.

Another way to say the same thing, is to notice that unlike a standard electrical network, on which the paths are discrete and fixed, the electrical path for the current that produces the muscle contraction is continuous over the whole 3-D structure of the heart muscle, and some leak out of it too, part of which is measured as EKG signals on the chest. Because the former, a standard electrical network is composed of discrete, enumerable paths, the information is given as the denumerable branches and nodes, while in the latter case (the heart) the information is a continuous current vector field.

Besides selecting which electrodes are turned on or off (connected or disconnected from the electrical power), the controlling microprocessor MP1 can also select one of a plurality of electric potentials (called voltages in US) to be connected to the field shaping electrodes. These voltages may vary as one out of a fixed set of available values, or may vary as a continuous of possible values within a minimum and maximum limits, depending on the design, both possibilities being covered by the invention. Varying the voltage at the field shaping electrodes, the device can adjust the electric field in the heart muscle, and therefore it can adjust the force applied on the propagating ions and ultimately the path of the electric current that is injected by the active electrodes. This offers an advantage over prior art, because out invention can better direct the electric current to the particular desirable target volume and avoid entering into undesirable volumes. Also, varying the voltage at the active electrodes, the device can adjust the current that is injected into the heart.

The Electric Field Lines.

The solution to the problem of controlling the path, in direction and speed, of the moving electric ions as they propagate through the heart muscle is found with a theoretical analysis of electric current propagation within an electric field. As a side remark, this is similar to the motion of an object by gravity within the gravitational field of the planet, which is vertical towards the center of the planet—assuming a perfectly spherically symmetrical Earth. All objects, unless prevented from falling by some means, do fall down in the direction of the center of the Earth, on a straight vertical line, that is, along the gravitational field lines. The earth gravitational field is set of lines radially pointing to its center, as most of the fields in FIG. 9. But FIG. 9 also displays two gravitational field lines next to an exaggerated large mountain, which, due to its large mass tilts the gravitational field lines sideways towards the mountain. An actual large mountain does, surprisingly enough, minutely deflects the gravitational field from its "normal" direction towards the center of the earth, and in amounts that are detectable with modern equipment (see an exaggerated off-radial displacement near the mountain at FIG. 9). This, of course, happens because the mountain attracts sideways. Exactly the same happens with the ions as they propagate through the heart muscle, causing a cel-by-cel contraction as they move, and also, as much as the mountain does attract a mass sideways, so does an electric field created by an externally positioned set of electric charges does change the path of the electric ions.

In the following the vector F is the force acting on an electrically charged particle of charge q and mass m, the vector E is the electric field at the position of same particle, and the vector a is the acceleration of the same particle. The following is then known from elementary physics 101, if not physics 99. Also we are adding the "(vector)" to the letters that are vectors because it is not possible to use the standard boldface convention in this publication.

$$F(\text{vector})=q \times E(\text{vector}), \text{ and}$$

$$F(\text{vector})=m \times a(\text{vector})$$

It follows that the force F, and consequently the acceleration a, are linearly correlated and proportional in magnitude, or, in other words, the acceleration is the force multiplied by a constant: 1/m, or the electric field E multiplied by a constant scalar q/m. From the acceleration being linearly proportional to the force F, which is, in turn, linearly proportional to the electric field E, it follows that the motion of an electrically charged particle starting from rest is a function of only the electric field lines and some scalar constants (q and m). The electric field can take more complex configurations than the gravitational field, because there are two types of electric charges (usually called positive and negative), while the gravitational field is due to only one type of gravitational charge (called mass, they all attract each other). FIGS. 10A, 10B, 10C, 10D and 10E display five types of simple electric field configurations: FIGS. 10A and 10B display two cases of field lines that are simpler to calculate, of two electric charges, in fact the configuration normally seen in introductory physics books. The field lines are the lines along which an electric charge moves if left unconstrained to move. In other words, the field lines control the flow path of the injected current. From this it follows that to shape the electric field lines is the same as to lay down the "roads" where the current will travel whenever charges are set free in the region. This notion of shaping the field lines to determine the current path is seldom used only because in most electric circuits the current (charge) is forced to follow the wires, the coils, the transistors, etc., with no place for an externally imposed electric field to have any effect. FIG. 10C shows a more complicated case with three charges. The reader is invited to observe the large change of the configuration of the field lines caused by the addition of this third charge, in particular the disappearance of the symmetry that is obvious in FIGS. 10A and 10B. FIGS. 10D and 10E display the effect of varying the value of the third charge. Again the reader is invited to ponder on the consequences of varying the values of the charges. Notice that both FIGS. 10D and 10E are asymmetric, yet the shape of the field lines is vastly different between them!

The electric field lines are distinctively unequal, very different shapes. Not displayed is also their strengths, which is also distinct, left out to simplify the figure. FIGS. 10 (A, B, C, D and E) illustrate the point of our invention: a method and a means to conform the electric field lines to the desired 3-D shape required for a most desirable electric ions path which determines the heart squeezing sequence. In fact, using the piquita of our invention, it is possible to even create a 3-D electric field which causes a better heart squeezing sequence than the sequence that happens in a normal, healthy heart, because a normal, typical, healthy heart does not actually follow the best possible sequence.

Taken together, controlling the direction and the magnitude of the current, our invention is capable of controlling the position and the magnitude of the squeezing sequence.

Introduction to the Mathematical Treatment of the Problem of the Best Electric Current Distribution Over the Heart Muscle.

The uniquiness theorem of Poisson's equation is a well known result in electrostatic. It has a few variations depending on the type of boundary conditions, but making a long story short, it states that if one has complete control of either the electric charges at all points on a closed surface, or else, if one has complete control of the electric potential at all points on a closed surface, then one has complete control on the electric field inside that closed surface. (see Reitz, Milford and Christy (1980), Jackson, (1975) or most any other introductory text in electromagnetic theory). This physical statement is related to the Dirichlet's principle DIRICHLET (n/d) In our case the stimulating device does NOT have total control, because it would be impossible to set voltages at unconstrained values (the electric energy source/battery is rather limited on its maximum output), nor do we have access and control over some surface that completely encloses the heart (or the brain, etc.), which means that not all desired vector fields are possible. Yet, adjusting the available electric potentials (voltages) over the available surface on the device in the vicinity of the desired volume it is possible to have a certain degree of control of the current vector field over the heart volume, and consequently to have more control on the path and speed of the injected electric electric charges and better results for the patient. This is even more correct when the piquita stimulator is, as is becoming more common nowadays, a three independent stimulators, one at the top right atrium, one at the bottom of each ventricle. Our invention does not create a total control on the field lines, our invention cannot create all arbitrary field shapes, but our invention can shape the field to a better conformation than old art which offered no control of it. In fact, to the best of the knowledge of the inventors, nobody before have ever tried to control the electric field shape on the heart muscle to control the current through it. Our invention cannot solve all heart problems, particularly broken hearts cannot be solved by our invention, but our invention is a step on the right direction and our invention increases the degree of control available to improve the heart functioning.

This mathematical theory indicates that our invention works better with either a larger area supporting electrodes (which approaches a totally containing surface) and also with just a few small electrodes spread apart, as in the two- and three-electrodes of current heart pacemaking, anchored as they are, at the top of the right atrium and bottom of each ventricle.

Therefore our invention is the use of a controlled charge distribution (or voltage, which is the same, because one determines the other) over as large an area as feasible, with the objective of adjusting the electric field lines over the heart muscle so that the injected current causes a downwards moving current from the top of the atrium to the boundary between the atrium and the ventricle, then either another current through the His bundle, right and left bundles and Purkinje fibers, or else simply another starting electric current originating on another implant at the bottom of the ventricle, possible if the cardiologist decides to use a two-electrodes pacemaking system. Moreover, the surface electrodes can be of either type 1 (active) or type 2 (field shaping). The first type of electrode can be either starting or finishing points for electric current paths, while the second type of electrodes is able to bend the field lines but not able to inject charges, because it is electrically insulated (though it can act via capacitive effect, as well known to the persons versed in the field of electrical engineering). Finally, given that the times involved are very long for electronics, a typical heart period being almost a full second and its P, Q, R, S and T waves lasting from a few to 10s milliseconds, while microsecond is easy in electronics, it is perfectly feasible to activate electrodes or either type (active or field shaping types) then turn them off sometime before the slowly moving electric current arrives at the electrode, therefore forestalling the establishing of a terminal point for a current. This can be dynamically adjusted to keep the current moving along a desired path, while never absorbing it. This selective adjusting of the ending points of an electric field line is effective in creating strong field lines with the use of electric charges near the initiation point of the current, which in turn is made to disappear as the current nears intermediate positioned electric charges, which may be substituted by other charges further along the desired path, all working as a carrot moving ahead of a running rabbit. Of course that the reverse action can be also created, of a same sign charge being introduced behind the moving current, in which case this same charge could be seen as akin to a whip at the back of the moving current, a horse-type incentive added to a rabbit-type one.

Two and three electrodes heart pacemakers are becoming common nowadays, and more electrodes may be used if a good reason for them is discovered, as our invention does. Even three anchored heart piquitas in three different places already open new possibilities for shaping the electric field; more than three offer even more possibilities.

DESCRIPTION AND OPERATION OF ALTERNATIVE EMBODIMENTS

Another possible variation for the Dirichlet's shirt is a long sleeve Dirichlet's shirt with electrodes at one or both sleeves, for cases of pain control, similar to TENS (Transcutaneous Electrical Neural Stimulation). For home use, if and when there were no concerns about the visual impression, it could be just the sleeve too.

Another possible variation for the Dirichlet's shirt is a wrist band adapted to electrically stimulate the nerves and muscles under it. Such a device may be useful as an adjunct to treatment of the carpal tunnel syndrome.

Another possible variation of the Dirichlet's shirt is for dental offices. In this case the Dirichlet's shirt would be a malleable sheet-style surface that conforms to either the full face of the patient or to part of the face of the patient, with electrodes both of the active type $140\_t1$ and of the field shaping type $140\_t2$. The active electrodes would preferably be of the positive polarity, and the negative polarity would be connected to the needle that is ready to inject anesthetics or to the drill that is about to drill the tooth, or to the tool that is going to be used to extract a nerve, etc. With this configuration a current would flow from the metallic part that is about to cause pain (the needle, the drill, the nerve extracting tool, etc.) to the positive active electrode on the outer surface of the mouth, through the nerve just ahead of the needle, the drill, the nerve extracting tool, etc. This electrical current would, as it is known, dampen the pain transmission at the nerve that is about to receive injury, because it is just ahead of the injuring element (the needle, the drill, the nerve extracting tool, etc.). The invention still uses field shaping electrodes for this variation, which would direct the current from the injuring element to the positive polarity active electrodes. Of course that the polarity could be reversed: positive polarity at the injuring element, and negative polarity at the active electrode.

Another variation of the first embodiment is a soft flat surface, similar to an ordinary bed sheet, which is adapted to be folded around the heart, just over the pericardium, that is, just around the heart, which is fitted with a plurality of electrodes, some or all of which are of the field shaping type. We call this variation the Dirichlet's pericardium cover. This variation of the main embodiment includes a battery and controlling electronics that is implanted somewhere in the patient's chest and connected to the electrodes by wires or other appropriate conducting means, similarly to any other implanted electrical stimulator. This variation is more efficient than the main embodiment in that the field shaping electrodes are closer to the intended volume where the electric field is to be maintained, but suffers from the need of surgery to implant it, also surgery to periodically replace the battery requiring another surgery, though simpler than the electrode sheet implant, because the battery would normally be located just under the patient's skin. The Dirichlets's pericardium cover is more effective than the Dirichlet's shirt because it is just near the heart, but the required surgery causes one to think twice (or even three or four times) before using it, in spite of it being more effective. On the other hand, in cases where the heart has to be exposed anyway, for other reasons, a Dirichlet's pericardium cover may be appropriate. Such a Dirichlet's pericardium cover has been developed and used in the heart of an unfortunate rabbit that was murdered for the experiment in 2014, or, as they say it, was humanly put to sleep (see LizhiXu, Igor R. Efimov et al. "3D multifunctional intergumentary membranes for spatiotemporal cardiac measurements and stimulation across the entire epicardium" Nature Comm Vol 5 Pg 3329 (March 2014), Colleen Clancy and Yang Xiang "Wrapped around the heart" Nature Vol 507 pg 43 (6 Mar. 2014), and Pierre Martin "Une membrane artificielle pour surveiller le coeur" La Recherche (1 Mai 2014)). LizhiXu and others did not use field shaping electrodes; to our knowledge the use of the $140\_t2$ electrodes was first described by the inventor and his collaborator Chong Il Lee (see U.S. Pat. No. 8,954,145, 10 Feb. 2015).

Another embodiment of our invention is application to DBS (Deep Brain Stimulation). In this application the objective is to disrupt the anomalous neurons firings that cause the tremor characteristic of Parkinson's disease, or of what is known as essential tremor. One of the possible solutions is to place an electrode on a chosen target area in the brain then superimpose a current of frequency around 200 Hz on it. FIG. 11 shows a brain-type stimulator we call picafina, similar in structure to prior art stimulators with 4 rings at their distal extremity (Butson and McIntyre (2006)) but with the equivalent electrode described for the heart piquita: field shaping and active electrodes. The objective for the Deep Brain Stimulator (DBS) is to adjust the electric field in the vicinity of the brain electric stimulator, which we call picafina or picafina-style stimulator, to the shape of the particular target volume, which could be the sub-thalamic nucleus (STN), the globus pallidus internus (GPi) or any other. Much effort has been put on the solution of this problem, the solution of which has evaded the practitioners of the art for decades—see, for example, Butson and McIntyre (2006). It can be seen at Butson and McIntyre (2006) that the best solution proposed is still a symmetric field. Such a symmetric field fail to offer a maximum electrical stimulation in any case, particularly when the electric stimulator happens to have been implanted off-center. As discussed by Butson and McIntyre (2006), this is, in fact, a most common occurrence, due to the small size of the target volumes and their location deep in the base of the brain (for DBS), which is also not directly observed by the surgeon, which inserts the electric stimulator through a one-cm diameter hole drilled at the top of the skull, from where she tries to guide the stimulator tip to the desired target. Our invention allows for more control of the electric field around the stimulator, which in turn, allows for better clinical results. More modern stimulators, e.g. the ones introduced by Sapiens Neuro (www.SapiensNeuro.com) a company that has been swallowed by Medtronic for a low price, and are capable of creating an asymmetric electric charge distribution in the target area, but fail to decouple the control of the electric field from the injection of the electric charges, therefore failing to maximize the results.

The electrodes for DBS can be of different size, of different shapes and also randomly distributed on the surface of the supporting structure or picafina, or they can be of uniform size and shape, perhaps to decrease manufacturing cost, for example, or to simplify the internal wiring, or any other reason. Given the small size of the electrodes, random shape of them is of smaller effect than their numbers, while the use of the two types of electrodes, active or type-1 electrodes and field shaping or type-2 electrodes are of major importance, given that the latter only change the electric field shape around the stimulator device.

The reader will notice that the DBS application is a natural adaptation of all that is described for the heart pacemaker, yet the DBS needs no time control of a sequential muscular contraction, so it is simpler to program and to use than the heart piquita. A multiplicity of electrodes, of variable shapes and sizes, each associated with a unique wire, which is used to select which electrode is turned on, which electrode is turned off, both for type-1 (active) and type-2 (field shaping). Likewise for the heart pacemaker, the DBS incarnation uses two types of electrodes: a first type, or active type, capable of injecting a current, and a second type, or field shaping type, which is insulated, not capable of injecting any current (though always there is a small leak current due to insulator imperfections), but which is much useful for creating the vector field around the electrode, which, in turn, determine the 3-D path for the injected current.

For DBS applications the invention has the advantage over existing devices that the field shaping electrodes are capable of keeping the electric charges injected by the active electrodes inside a much smaller volume than can be achieved today. This is very important because the Lara theory of Parkinson's Disease predicts that the origin of the tremor characteristic of the disease is in a region much smaller than currently accepted. It is the opinion of the inventor that electrically stimulating a large volume as is done by existing electric stimulators is likely to both cause side effects (a known fact) but also likely to eventually develop self sustaining Ramon y Cajal loops. These loops are known as Hebbian loops because D. O. Hebbs is erroneously considered the proposer of the loops as the elementary units of brain activity, the site of memory and other processes. Donald Hebb wrote a beautiful and convincing prose, but he was not the first to come up with the loops. The new loops created by the injected stimulation current, in turn, may cause tremors of their own unless stopped by the use of higher voltages, which explains the known fact that often the voltages have to be increased with time for the same patient, which is considered an unavoidable type of resistance development but that the Lara theory explains as the creation of new Ramon y Cajal loops that could be avoided if the stimulated volume were smaller.

Another possible application for the invention is for appetite control. In this application there are two possibilities: electrical stimulation on the stomach, and brain stimulation at the locations which are known to control the appetite. In the former case the added electrical stimulation may be turned on before a meal, and the electrodes are selected to affect the neurons that send information to the brain regarding the current amount of food in the stomach, which in turn modulate the appetite. If the stimulation is capable to fool the brain, the individual will feel a decreased urge for food, eat less, and lose weight on the long run. This has been used in humans already. The second case, brain stimulation to control the appetite has been only used in animals so far, and with success. For stomach stimulation the shape of the stimulator should be a flat shape to conform to the curvature of the stomach and its enervations, a variation of what we call planarium. For direct brain control it may be similar to the DBS.

Another possible application is for cortical brain stimulation, in which case the stimulator has a flat shape to adjust to the cortical application. We call planarium this sheet-like deformable stimulator.

Another possible application is for pain control, an improvement of a known device known as TENS (Transcutaneous Electrical Neural Stimulation). In this application the objective is to control superficial pain, as skin pain, and it has used for deeper pain too, as muscle pain. The area (here it is really an area, the surface area of the skin in question, not what the neurologists call area, which is a volume) in question is in this case surrounded by electrodes attached to the skin, from which there is a current flow. Old art used large electrodes, which did not allow for a control of the current path. In this case our invention discloses a large number of small electrodes which are on the surface of the applied patch. Likewise the heart pacemaker, these small electrodes are numbered and individually activated by their dedicated wires which is under control of the controlling electronics, are of two types (type-1, or active, and type-2, or field shaping), and can likewise be turned on at any of a plurality of voltages/currents or off (zero voltage/current). With a wise selection of the active electrodes, it is possible for the medical practitioner to ameliorate the pain felt by the patient in a more effective way than currently used TENS devices. FIGS. 5A and 5B show how to control the depth of penetration of the stimulating current using the field shaping electrodes $140\_t2$.

The individual electrodes, which in the main embodiment may be randomly spread on the supporting structure (picafina), and are of various shapes and sizes, can be all of the same shape and/or same size, and/or can be arranged on an orderly arrangement too. In such a case the advantage of maximal symmetry breaking is not achieved, but some partial symmetry breaking is still obtained with the selection of particular electrodes as the points from which to initiate the stimulation, and the selection of other particular (insulated) electrodes from which to originate the field shaping lines. Cost and other factors could determine a simpler regular electrode arrangement. More orderly arrangements of the electrodes than the arrangement disclosed in the main embodiment, which provides maximal advantage, are still in the scope of the invention.

Persons acquainted with the art of symmetry will recognize that for very small electrodes with small spacing between each, there is little gain if compared with larger electrodes of variable shape and sizes, as particular sets of smaller electrodes can approximately create the shape of a larger electrode of any arbitrary shape. Cost and programming time may dictate one type of another of electrode, and their size and placement, while these variations are still covered in the scope of the invention.

The relative distribution of the electrodes of type-1 and type-2 (current injecting electrodes and electric field shaping electrodes, or magnitude and direction determining electrodes) is random in the main embodiment of this invention, but it is possible to alternate electrodes from type-1 to type-2, then type-1 again, etc., when the electrodes are of the same size and orderly distributed on the surface of the stimulating piquita, picafina and their variations devices.

One interesting regular pattern for the electrodes is the hexagonal pattern, which is shown in FIG. 12A, and other variations of it, as the octagonal pattern, shown in FIG. 12B. These are some two possibilities of the many, with the surrounding electrodes of the active type and the center (hexagonally shaped, octagonal shaped, etc), and the electrode of the field shaping type surrounding as needed. Other combinations are possible. It is, of course, possible to use only hexagons, because they completely fill a 2-D space. In this case type-1 and type-2 electrodes would alternate, or they could also be random. This particular electrode distribution is symmetrical, which is a departure from the main embodiment, but, given that the electrodes are small, most asymmetric shapes can be approximated. Variations of FIGS. 12A and 12B are reversing black with white electrodes (that is, reversing active and field shaping-type), or making them random, each electrode, regardless of their position, center hexagon or one of the surrounding six parallelepid, being assigned randomly to be active or field shaping. In later use, it is a computer program that determines, from mathematical calculations, which of the electrodes are on and off, in order to create the desired field shape.

Persons familiar with the art understand that the hexagonal pattern displayed at figure FIG. PPA15*b* is just one of the many possibilities. Triangular arrays square arrays, rectangular arrays, and others are possible, these being examples of arrays that completely fill the space. But the individual units do not have to even completely fill the available space, because maximal asymmetry (maximal lack of symmetry, or maximal symmetry breaking) is achieved with random distribution of electrodes.

FIG. 13 shows another interesting configuration, in which the field shaping electrodes, otherwise indicated as **140_*t*2, are there indicated as 140_*t*3, differing from the 140_*t*2 field shaping electrodes in that 140_*t*3 electrodes are buried underneath the other electrodes, both active and field shaping ones. When 140_*t*3** are buried, all the surface electrodes may be active, which increase the surface available from which to inject current—as there is no need to put field shaping electrodes on the surface. At the same time, the available surface for the field shaping electrodes is also larger when they (the field shaping electrodes) are buried. The subterranean or buried configuration increases the available surface for both active and field shaping type of electrodes, causing an improvement on the device over previously described field shaping electrodes.

Note that FIG. 13 displays a cut view on the yz-plane (coronal), of a picafina with axis along the y-axis. Typically there are 4-8 electrodes at a particular y-coordinate comprising an angle slightly <90 dgs (4 electrodes) or slightly <45 dgs (8 electrodes). In this figure **140_*t*1 are the active electrodes, which are the ordinary electrodes at the surface, and 140_*t*3 are the new subterranean passive electrodes underneath the active electrodes. 140_*t*3 are the new electrodes, which are electrically insulated from their surroundings, therefore incapable of injecting electric charges in their surroundings, this being why they can be under the surface, which is not the case for the normal, or active electrodes 140_*t*1. 140_*t*3 are preferably made with supercapacitor technology to maximize the electric charge on them, therefore maximizing the electric field projected in the space surrounding the picafina, which is subjected to electrical stimulation by the active electrodes 140_*t*1 at the surface. Passive electrodes may be at the surface of the devices, next to the active electrodes, or they may be under the active electrodes, in the configuration known as subterranean passive electrodes 140_*t*3**, which is the one depicted here.

CONCLUSION, RAMIFICATIONS, AND SCOPE OF INVENTION

Another way to see the control of the paths of the current in the heart, or the extent of electrical stimulation in brain DBS, etc., is to look at the active electrodes determining the magnitude (and also the direction in a limited way too, because the active electrodes also contribute to the electric field vector) and the field shaping electrodes determining the direction and speed only of the current injected by the former, active electrodes. In this view one considers the stimulating current as a vector which follows the electric field lines.

Other options are possible for the marker 140-*tm* that indicates the angular position of the piquita as implanted. For example, all the electrodes may have enough X-ray opacity to show in the fluoroscopic images taken during the heart pacemaker implantation. Or one or more or the anchoring arms 131 may be smaller (or larger), or each anchoring arm may be of a different length and/or diameter, to allow their identification.

The main embodiment for heart stimulation uses a simple version of stimulation, which is fixed and continuous, of the type of the old heart pacemakers. It is possible to have stimulation on demand too, as many current pacemakers have, which is based, for example, on activating the stimulation only when the natural pacemaker becomes insufficient, or stops, or becomes erratic. This is called stimulation on demand, easily incorporated in our invention that already contains a microprocessor capable of implementing such decisions. Such extensions are part of the current art of heart pacemakers and may or may not be incorporated in our invention. Our invention is independent of stimulation on demand.

Another extension to the invention disclosed in my provisional application dated May 2011 and real application dated May 2012 (patent application Ser. No. 13/470,275) is the use of electrodes just below the skin, which can be of the field shaping type (type-2 **140_*t*2), or active (type-1 140_*t*1) electrode or both types of electrodes (140_*t*1 and 140_*t*2**). Such electrodes can create a much stronger boundary condition (in the mathematical sense, a la Dirichlet) then the single, or even double and triple piquita implants, because the available surface is much larger in this case when compared with the available total surface of the type-2 electrodes on the initial disclosure, even using the currently used three electrodes at the right atrium and one each at each ventricle. The piquita have severe limitations on their sizes and locations, while the surface electrodes can have a much large surface area and can encompass a much larger total area. In fact, it is in principle possible, though impractical to implement, to have an almost 4-pi steroradians surface around the heart, as a tight garment weared by the patient with just two holes for the eyes, two holes for the ears and one for the nose, with three more temporarily open hole for the mouth, penis and anus, with an almost as effective garment just around the chest, which could encompass a 3-dimensional angle barely smaller that the total skin-covering device, while being eminently feasible. Such chest wearing skin could be totally external, including the necessary battery, which solves the crucial problem of battery lifetime of implantable devices.

Other variations and modifications are possible for neural electrical stimulation at the head (brain), as for DBS, etc., where it is advantageous to have field shaping electrodes near the holes drilled to insert the implant (burr hole for DBS, etc.), on one or both sides of the skull and on one or both sides of the dura matter. Field shaping electrodes should also exist on the connecting wires that lead to the electrodes (if any) or on the surface of the picafina (the approximately 1.5 mm diameter cylindrical stiff support that is inserted in the brain from the burr hole at the top of the skull for DBS, etc.) field shaping electrodes may also be placed underneath the active electrodes, and these field shaping electrodes underneath the active electrodes are called from now on subterranean field shaping electrodes. The subterranean field shaping electrodes are electrically insulated from the active electrodes. Such subterranean field shaping electrodes being independently connected to the electrical energy source, they can be at a higher or lower electrical potential than the active electrodes on top of them, besides holding a much larger electric charge for the same value of applied electric potential, if made with supercapacitor technology.

Another variation that can be made is to consider that the influence of the field shaping electrodes 140-$t2$ on the electric field is proportional to the electric charge accumulated on them. This electric charge accumulated on the electrodes 140-$t2$, in turn, can be increased if the field shaping electrodes are constructed to increase the electric charge accumulated on them. The accumulated electric charge on the field shaping electrodes 140-$t2$ can be vastly increased by constructing them as capacitors, and, more precisely, with the technology used for the super-capacitors. This is easy to do with existing technology used for printed circuits and micro-fabrication, and is actually a well developed branch of electronics today, where capacitors of several Farads have been manufactured.

For the non-technical reader, the large capacitance can be a consequence of several factors, one of which is a larger surface area of the electrode. The surface, and not the volume, is the figure of merit here, because freely moving electric charges on a conducting body always stay at the surface of the body—in order to maximize the distance between them: just make a drawing and think where the electric charges will go once set free in the body (they are doing their best to stay away from each other), then keep in mind that your discovery, if you did not knew it already is mathematically described and predicted by Gauss' law that says that the electric field inside the volume of an electric conductor is always zero. This is a known fact in the trade, part of the first courses in the electricity part of physics. This is so because the accumulated charges, being as they are by necessity of the same sign, are necessarily repelling each other, so they prevent more charge from coming in their vicinity. Consequently, the surface area is larger, then a larger amount of charge can fit in, so to say. Supercaps are conducting bodies with extremely large porosity, which increases the total surface area. An example for the non-initiated is a 2-D variation: a labyrinth, of the type seen in puzzles, where one must find a path from a entrance starting point to a finish exit, has a much longer wall length than a simple hallway leading from the entrance to the exit! Well, the surface area of a 3-D body is the same situation of the labyrinth, just in 3-D, where, as the dimension increased from 2 to 3, what is the wall length in 2-D becomes a surface area in the 3-D case. Ultimately the porous surface of the supercap can store more electric charges than a box-like electrode, and then, because the electric field is dependent of the total accumulated charge (and not on the electric potential, a.k.a. Voltage in US), the electric field created by the supercap is stronger, in magnitude, than the equivalent electric field created by a box-like field shaping electrode for the same electric potential (voltage as it is known in US). The battery can set the electric potential (say 2 V), and for the same electric potential there is more charge on the supercap electrode (porous construction) then in the box-like electrode.

More variations can be conceived if one considers that if the general method of the field shaping electrodes is to have electric charges at widely separated positions, and preferably close to the point of interest, then each one have a large different contribution from the others, because each of which contribute for the electric field in the heart muscle (miocardium) from different directions. While the active electrodes are turned off after the stimulating pulse is injected, the same is not true for the field shaping electrodes, which continue on. It follows that the wires that connect the battery/controlling electronics to the field shaping electrodes anchored in the heart wall stay on, which in turn means that they hold distributed electric charges (this can be seen as a capacitance). Since the wire capacitance is small, the actual charge distributed along their length is small, as given by the equation that describes the relationship between the applied electric potential (voltage), the capacitance and the charge:

$$Q = C \cdot V,$$

so, for a fixed V, a small capacitance means a small charge. Then, because the electric field is directly proportional to the charge Q, it follows that the influence of the wire is small, given that the charge on them is small. A supercapacitor, on the other hand, increasing C also increases Q and therefore the effect on the electric field, this being the reason for the several supercapacitors placed at several locations along the wires leading to the stimulators.

Each of these supercapacitors should be controlled individually by the controlling electronics, perhaps by a dedicated wire, perhaps by using a digital addressing system to select them. With these supercapacitors, larger charges can be stored at their positions and consequently a larger influence can be caused on the value (magnitude and direction) of the electric field E at the heart walls (miocardium).

These wires or cables are the wires normally used for the implant. They ran from the subclavian vein (where they are inserted) down the blood vessel system to at least the upper part of the right atrium (C1), or to this and also, with a separate wire C2, to the right ventricle, as in CRT (Cardiac Resynchronization Therapy), or to these and to the left ventricle (not shown) also in cardiac resynchronization therapy. The position of these wires is relatively fixed, in the sense that the cardiologist have virtually no control on their positions. More wires can be introduced, either from other veins, or using surgery. Using surgery, perhaps laparoscopy (less invasive surgery via small holes) more wires and field-creating supercaps can be placed near the heart at other locations than the wires coming from the subclavian vein.

In any of these cases, it may be more advantageous to use another, separate and larger supercapacitor SC_energy (not shown), capable of storing enough charge for one or a few days of operation, that is, enough charge for one or a few days of field shaping electrode functioning. SC_energy could then be recharged at night using a pair of coils, one acting as an emitting antenna outside the chest, the other acting as a receiving antenna inside the body, which would then be rectified and manipulated by electronics as needed to keep SC_energy charged for the next day or days.

One skilled in the relevant art, however, will readily recognize that the invention can be practiced without one or more of the specific details, or with other methods, etc. In other instances, well known structures or operations are not shown in detail to avoid obscuring the features of the invention. For example, the details of the wiring can be realized in several different ways, as coiled wires, as printed circuit wires, etc., many or most of which are compatible with the invention, and therefore the details of these, and other details are not included in this patent disclosure. The invention also requires electronic circuits to adjust the electric potentials to the desired values (or to adjust the "voltage" as it is said in USA), which electronic circuits are not included in this patent application because these are well known in the art of electronics. These electric potential ("voltages") adjustments can be made with potentiometers and the like, using hardware, or they can be done at a distance using radio waves or other waves, for example using blue-tooth technology (no pun intended) etc., all well known variations that are not disclosed for being well known in the art.

REFERENCES

Julia Buhlmann, L. Hofmann, Peter A. Tass, C. Hauptmann "Modeling of a segmented electrode for desynchronizing deep brain stimulation" Frontier in Neuroeng. V 4, article 15 (December 2011)

Butson and McIntyre (2006). Christopher R. Butson and Cameron C. McIntyre "Role of electrode design on the volume of tissue activated during deep brain stimulation" Journal of Neural Engineering, vol. 3, pgs. 1-8 (2006)

Christopher Butson, Cameron McIntyre "Current steering to control the volume of tissue activated during deep brain stimulation", Brain stimulation V. 1, pg. 7-15 (2008) [currently 2013/Articles/ArticlesFromUCLA Chong Il Lee and Sergio Lara Pereira Monteiro (2011) "Method and means to address and make use of multiple electrodes for measurements and electrical stimulation in neurons and other cells including brain and heart" U.S. patent application Ser. No. 13/053,137, Mar. 21, 2011, not yet published.

Chong Il Lee (2010) "Method and means for connecting a large number of electrodes to a measuring device" US patent application number 20100079156, published Apr. 1, 2010

Chong Il Lee and Sergio Lara Pereira Monteiro (2010) "Method and means for connecting and controlling a large number of contacts for electrical cell stimulation in living organisms" U.S. patent application number 20100082076, published Apr. 1, 2010.

Clancy (2014) Colleen Clancy and Yang Xiang "Wrapped around the heart" Nature Vol 507 pg 43 (6 Mar. 2014).

DIRICHLET—http://en.wikipedia.org/wiki/Dirichlet_principle

Kenneth Follett et al. "Pallidal versus Subthalamic Deep-Brain Stimulation for Parkinson's Disease", N Engl J Med. V 362, pg 2077, (2010)

Jackson (1975) Jackson "Classical Electrodynamics" Wiley.

JamilleHetke_Kipke_Pellinen_Anderson_ModularMultichannelMicroelectodeArrayEtc_USPTO-PatPubl-US2007-0123765_070531

LizhiXu (2014) LizhiXu, . . . Igor R. Efimov et al. "3D multifunctional integumentary membranes for spatiotemporal cardiac measurements and stimulation across the entire epicardium" Nature Comm Vol 5 Pg 3329 (March 2014).

Martin (2014) Pierre Martin "Une membrane artificielle pour surveiller le coeur" La Recherche (1 Mai 2014).

Medtronic (n/d) Medtronic website with info on DBS leads. http://professional.medtronic.com/pt/neuro/dbs-md/prod/dbs-lead-model-3387/index.htm http://professional.medtronic.com/pt/neuro/dbs-pd/prod/dbs-lead-model-3391/index.htm Reitz, Milford & Christy (1980), John Reitz, Frederick Milford, Robert Christy "Foundations of Electromagnetic Theory" $3^{rd}$ edition, 1980.

Thaler (2003) Malcolm S. Thaler "The Only EKG Book You'll Ever Need", Lippincott Williams & Wildins, $4^{th}$ ed. (2003).

The invention claimed is:

1. An electrical stimulator device composed of:
a minimum of one type-1 electrode supported by a first supporting device formed as a rigid penetrating device that is inserted in an animal,
whereas the type-1 electrodes are adapted to apply electrical stimulating current to the animal,
wherein the type-1 electrode that is supported by the first supporting device formed as the rigid penetrating device that is capable of being inserted into at least part of the volume inside the animal or inside an organ of the animal, is adapted to inject an electric current in its surroundings,
wherein the first supporting device formed as the rigid penetrating device is adapted to be inserted into at least part of the volume inside the animal or inside an organ of the animal,
wherein the first supporting device formed as the rigid penetrating device is a pain-inflicting device which device causes pain on the animal, the pain-inflicting device belonging to one of the elements of the set:
1. a needle used to inject anesthetics near the nerves and teeth of the animal,
2. a sharp pointed device used to scratch the teeth surface to inspect for cavities,
3. a Jacquette Scaler,
4. a Sickle Scaler,
5. an explorer #23,
6. a tartar remover scaler,
7. a root canal spreader,
8. a margin trimmer,
9. a gracey periodontal curette,
10. a periodontal probe,
11. a Heidman spatula,
12. a drill used to take away decayed teeth tissues,
13. any of a multiplicity of tools used to extract a nerve for a root canal treatment
14. any spatula or probe or drill or other dental tool used in dental procedures.

2. The electrical stimulator device of claim 1 further provided with one or a plurality of type-2 electrodes, which are attached to a second supporting device whereas the second supporting device is either a volumetric structure, or a surface structure or a linear structure, wherein the surface structure may be planar or non-planar.

3. The electrical stimulator device of claim 2 wherein the second supporting device contains type-1 electrodes which are of a polarity that is opposite to the polarity of the type-1 electrodes located at the first supporting device formed as the rigid penetrating device, or are of a polarity that is the same as the polarity of the type-1 electrodes located at the first supporting device formed as the rigid penetrating device.

4. The electrical stimulator device of claim 2 wherein the second supporting device is provided with velcro or buttons or zippers or glue to be attached to precise locations on the animal.

5. The electrical stimulator device of claim 2 wherein the second supporting device is shaped as a head cover that is adapted to be worn on a head of the animal.

6. The electrical stimulator device of claim 2 wherein the second supporting device comprises part of a scarf that is adapted to be worn by the animal.

7. The electrical stimulator device of claim 2 wherein the second supporting device is adapted to be worn on a neck of the animal.

8. The electrical stimulator device of claim 1 wherein the rigid penetrating device is a needle adapted to inject anesthetics in preparation for a dental procedure on the animal.

9. The electrical stimulator device of claim 1 wherein the rigid penetrating device is a drill adapted to drill a tooth as part of a dental procedure on the animal.

10. The electrical stimulator device of claim 1 wherein the rigid penetrating device is a pointed metallic probe adapted to probe a tooth as part of a dental procedure on the animal, as for finding cavities.

11. The electrical stimulator device of claim 1 wherein the rigid penetrating device is a tool adapted at extracting a nerve from the animal.

12. The electrical stimulator device of claim 2 wherein the second supporting device is shaped as a curved surface that is adapted to be worn on a face of a head of the animal.

13. The electrical stimulator device of claim 2 wherein the second supporting device is shaped as a cheek cover that is adapted to be worn on a head of the animal.

14. A method of the electrical device of claim 1, with a minimum of one type-1 electrode supported by a first supporting device formed as a rigid penetrating device that is inserted in an animal, the method comprising:
- providing the first supporting device formed as the rigid penetrating device to physically support the electrical stimulation device of claim 1,
- providing a minimum of one type-1 electrode supported by the first supporting device formed as the rigid penetrating device that is inserted in the animal,
- providing the electronics circuits to cause the type-1 electrodes to be able to apply electrical stimulating current to the animal,
- providing the minimum of one type-1 electrode with the necessary wires and electrical connections that that are supported by the first supporting device formed as the rigid penetrating device that is capable of being inserted into at least part of the volume inside the animal or inside an organ of the animal, that is adapted to inject an electric current in its surroundings,
- providing the at least one first supporting device formed as the rigid penetrating device with a shape that adapted to be inserted into at least part of the volume inside the animal or inside an organ of the animal,
- choosing the at least one first supporting device formed as the rigid penetrating device that is a pain-inflicting device which device causes pain on the animal, the pain-inflicting device being one of the elements of the set:
  1. a needle used to inject anesthetics near the nerves and teeth of the animal,
  2. a sharp pointed device used to scratch the teeth surface to inspect for cavities,
  3. a Jacquette Scaler,
  4. a Sickle Scaler,
  5. an explorer #23,
  6. a tartar remover scaler,
  7. a root canal spreader,
  8. a margin trimmer,
  9. a gracey periodontal curette,
  10. a periodontal probe,
  11. a Heidman spatula,
  12. a drill used to take away decayed teeth tissues,
  13. any of a multiplicity of tools used to extract a nerve for a root canal treatment
  14. any spatula or probe or drill or other dental tool used in dental procedures.

15. The method of the electrical device of claim 14, wherein the electrodes are one or more electrodes from a group composed of: (1) the type-1 electric charge injecting electrode, (2) a type-2 field shaping electrode,
wherein the type-2 field shaping electrodes of the electrical stimulation device are configured to apply a force on either the propagating electric charges injected in the animal by the electrical stimulation device, or electric charges naturally produced by the animal.

16. The method of claim 14 further comprising at least one electrode of the group: (1) type-1 stimulating electrodes and (2) type-2 field-shaping electrodes,
whereas the at least one electrode belonging to one of the elements (1) or (2) of the group above is located at a second supporting device located at a position different than the position of the first supporting rigid penetrating device.

17. The method of claim 14 wherein,
the first supporting device formed as the rigid penetrating device is capable of causing discomfort or pain on the animal where the first supporting device formed as the rigid penetrating device is applied.

18. The method of the electrical device of claim 14,
wherein the type-2 field shaping electrodes of the electric stimulating device are configured to apply a force on either the propagating electric charges injected in the animal by the electric stimulation system, or electric charges naturally produced by the animal.

19. The method of claim 14 further comprising additional type-2 field-shaping electrodes coupled to a skin of the animal in which the electric stimulating device is implanted.

20. A method of applying electrical stimulation to tissues of an animal which consists of first device and a second device, wherein,
the first device is a rigid penetrating device adapted at being inserted in the animal, or in a cavity of the animal, or in a tissue of the animal, or in a part of the animal,
the second device is a malleable sheet-like structure adapted to conform to a full external surface of the animal or to part of the external surface of the animal, or to a full internal surface of the animal, or to part of the internal surface of the animal.

* * * * *